US010070800B2

(12) United States Patent
Cornish et al.

(10) Patent No.: US 10,070,800 B2
(45) Date of Patent: Sep. 11, 2018

(54) IMPEDANCE MEASUREMENT PROCESS

(71) Applicant: Impedimed Limited, Pinkenba, Queensland (AU)

(72) Inventors: Bruce Herbert Cornish, Greenbank (AU); Brian John Thomas, West End (AU); Jye Geoffrey Smith, Drewvale (AU)

(73) Assignee: IMPEDIMED LIMITED, Pinkenba, Queensland (AU)

( * ) Notice: Subject to any disclaimer, the term of this patent is extended or adjusted under 35 U.S.C. 154(b) by 315 days.

(21) Appl. No.: 14/963,018

(22) Filed: Dec. 8, 2015

(65) Prior Publication Data

US 2016/0089051 A1 Mar. 31, 2016

Related U.S. Application Data

(63) Continuation of application No. 12/672,893, filed as application No. PCT/AU2008/001145 on Aug. 7, 2008.

(30) Foreign Application Priority Data

Aug. 9, 2007 (AU) .................................. 2007904287

(51) Int. Cl.
*A61B 5/05* (2006.01)
*A61B 5/053* (2006.01)
*A61B 5/00* (2006.01)

(52) U.S. Cl.
CPC ............ *A61B 5/053* (2013.01); *A61B 5/7203* (2013.01); *A61B 5/7282* (2013.01); *A61B 5/0537* (2013.01); *A61B 5/4331* (2013.01); *A61B 5/444* (2013.01); *A61B 2562/0214* (2013.01); *A61B 2562/046* (2013.01)

(58) Field of Classification Search
CPC ...... A61B 5/053; A61B 5/7203; A61B 5/7282
USPC ........................................................ 600/547
See application file for complete search history.

(56) References Cited

U.S. PATENT DOCUMENTS

| 3,851,641 A | 12/1974 | Toole |
| 3,866,600 A | 2/1975 | Rey |
| 4,082,087 A | 4/1978 | Howson |
| 4,169,463 A | 10/1979 | Piquard |

(Continued)

FOREIGN PATENT DOCUMENTS

| EP | 0 339 471 A2 | 11/1989 |
| EP | 0 581 073 A2 | 2/1994 |

(Continued)

OTHER PUBLICATIONS

English Translation of CN1180513A published May 6, 1998.
(Continued)

*Primary Examiner* — Daniel Cerioni
(74) *Attorney, Agent, or Firm* — Knobbe, Martens, Olson & Bear, LLP

(57) ABSTRACT

A method for use in performing impedance measurements on a subject. The method includes, in a processing system, determining at least one first impedance value, measured at a site using a first electrode configuration, determining at least one second impedance value, measured at the site using a second electrode configuration, and determining the presence, absence or degree of an anomaly using the first and second impedance values.

21 Claims, 15 Drawing Sheets

(56) References Cited

U.S. PATENT DOCUMENTS

| | | |
|---|---|---|
| 4,836,214 A | 6/1989 | Sramek |
| 4,890,630 A | 1/1990 | Kroll et al. |
| 4,924,875 A | 5/1990 | Chamoun |
| 5,020,541 A | 6/1991 | Marriott |
| 5,101,828 A | 4/1992 | Welkowitz et al. |
| 5,184,624 A | 2/1993 | Brown et al. |
| 5,233,982 A | 8/1993 | Kohl |
| 5,272,624 A | 12/1993 | Gisser et al. |
| 5,282,840 A | 2/1994 | Hudrlik |
| 5,284,142 A | 2/1994 | Goble et al. |
| 5,335,667 A | 8/1994 | Cha et al. |
| 5,351,697 A | 10/1994 | Cheney et al. |
| 5,353,802 A | 10/1994 | Ollmar |
| 5,381,333 A | 1/1995 | Isaacson et al. |
| 5,390,110 A | 2/1995 | Cheney et al. |
| 5,421,345 A | 6/1995 | Lekholm et al. |
| 5,423,326 A | 6/1995 | Wang et al. |
| 5,427,113 A | 6/1995 | Hiroshi |
| 5,454,377 A | 10/1995 | Dzwonczyk et al. |
| 5,469,859 A | 11/1995 | Tsoglin et al. |
| 5,526,808 A | 6/1996 | Kaminsky |
| 5,575,929 A | 11/1996 | Yu et al. |
| 5,611,351 A | 3/1997 | Sato et al. |
| 5,615,689 A | 4/1997 | Kotler |
| 5,626,146 A | 5/1997 | Barber et al. |
| 5,735,284 A | 4/1998 | Tsoglin et al. |
| 5,792,073 A * | 8/1998 | Keefe ............... A61B 5/121  600/559 |
| 5,876,353 A | 3/1999 | Riff |
| 5,947,910 A | 9/1999 | Zimmet |
| 5,957,861 A | 9/1999 | Combs et al. |
| 5,964,703 A | 10/1999 | Goodman et al. |
| 6,115,626 A | 9/2000 | Whayne et al. |
| 6,129,666 A | 10/2000 | DeLuca et al. |
| 6,167,300 A | 12/2000 | Cherepenin et al. |
| 6,253,100 B1 | 6/2001 | Zhdanov |
| 6,280,396 B1 | 8/2001 | Clark |
| 6,308,097 B1 | 10/2001 | Pearlman |
| 6,376,023 B1 | 4/2002 | Mori |
| 6,432,045 B2 | 8/2002 | Lemperle et al. |
| 6,459,930 B1 | 10/2002 | Takehara et al. |
| 6,469,732 B1 | 10/2002 | Chang et al. |
| 6,472,888 B2 | 10/2002 | Oguma et al. |
| 6,501,984 B1 | 12/2002 | Church et al. |
| 6,511,438 B2 | 1/2003 | Bernstein et al. |
| 6,512,949 B1 | 1/2003 | Combs et al. |
| 6,516,218 B1 | 2/2003 | Cheng et al. |
| 6,522,910 B1 | 2/2003 | Gregory |
| 6,551,252 B2 | 4/2003 | Sackner et al. |
| 6,556,001 B1 | 4/2003 | Wiegand |
| 6,561,986 B2 | 5/2003 | Baura et al. |
| 6,564,079 B1 | 5/2003 | Cory et al. |
| 6,602,201 B1 | 8/2003 | Hepp et al. |
| 6,615,077 B1 | 9/2003 | Zhu et al. |
| 6,636,754 B1 | 10/2003 | Baura et al. |
| 6,658,296 B1 | 12/2003 | Wong et al. |
| 6,725,089 B2 | 4/2004 | Komatsu et al. |
| 6,763,263 B2 | 7/2004 | Gregory et al. |
| 6,788,966 B2 | 9/2004 | Kenan et al. |
| 6,790,178 B1 | 9/2004 | Mault et al. |
| 6,807,443 B2 | 10/2004 | Keren |
| 6,829,501 B2 | 12/2004 | Nielsen et al. |
| 6,829,503 B2 | 12/2004 | Alt |
| 6,840,907 B1 | 1/2005 | Brydon |
| 6,936,012 B2 | 8/2005 | Wells |
| 6,940,286 B2 | 9/2005 | Wang et al. |
| RE38,879 E | 11/2005 | Goodman et al. |
| 6,980,852 B2 | 12/2005 | Jersey-Willuhn et al. |
| 7,065,399 B2 | 6/2006 | Nakada |
| 7,079,889 B2 | 7/2006 | Nakada |
| 7,096,061 B2 | 8/2006 | Arad |
| 7,122,012 B2 | 10/2006 | Bouton et al. |
| 7,149,573 B2 | 12/2006 | Wang |
| 7,169,107 B2 | 1/2007 | Jersey-Willuhn et al. |
| 7,184,820 B2 | 2/2007 | Jersey-Willuhn et al. |
| 7,184,821 B2 | 2/2007 | Belalcazar et al. |
| 7,186,220 B2 | 3/2007 | Stahmann et al. |
| 7,233,823 B2 | 6/2007 | Simond et al. |
| 7,251,524 B1 | 7/2007 | Hepp et al. |
| 7,288,943 B2 | 10/2007 | Matthiessen et al. |
| 7,313,435 B2 | 12/2007 | Nakada et al. |
| 7,317,161 B2 | 1/2008 | Fukuda |
| 7,336,992 B2 | 2/2008 | Shiokawa |
| 7,440,796 B2 | 10/2008 | Woo et al. |
| 7,496,450 B2 | 2/2009 | Ortiz Aleman et al. |
| 7,603,158 B2 | 10/2009 | Nachman |
| 7,603,171 B2 | 10/2009 | Eror et al. |
| 7,628,761 B2 | 12/2009 | Gozani et al. |
| 8,068,906 B2 | 11/2011 | Chetham |
| 8,744,564 B2 | 6/2014 | Ward |
| 2001/0051774 A1 | 12/2001 | Littrup |
| 2002/0022773 A1 | 2/2002 | Drinan |
| 2002/0106681 A1 | 8/2002 | Wexler |
| 2002/0138019 A1 | 9/2002 | Wexler |
| 2002/0183645 A1 * | 12/2002 | Nachaliel ............ A61B 5/0536  600/547 |
| 2003/0004403 A1 | 1/2003 | Drinan |
| 2003/0009111 A1 | 1/2003 | Cory |
| 2003/0105410 A1 | 6/2003 | Pearlman |
| 2003/0120182 A1 | 6/2003 | Wilkinson et al. |
| 2003/0173976 A1 | 9/2003 | Wiegand |
| 2003/0176808 A1 | 9/2003 | Masuo |
| 2003/0216664 A1 | 11/2003 | Suarez |
| 2004/0073127 A1 | 4/2004 | Istvan et al. |
| 2004/0073130 A1 | 4/2004 | Bohm |
| 2004/0116819 A1 | 6/2004 | Alt |
| 2004/0181163 A1 | 9/2004 | Acumen |
| 2004/0210158 A1 * | 10/2004 | Organ ............... A61B 5/0536  600/547 |
| 2004/0220632 A1 | 11/2004 | Burnes |
| 2004/0234113 A1 | 11/2004 | Miga |
| 2004/0242989 A1 | 12/2004 | Zhu |
| 2004/0243018 A1 * | 12/2004 | Organ ............... A61B 5/053  600/547 |
| 2004/0260167 A1 | 12/2004 | Leonhardt |
| 2004/0267333 A1 | 12/2004 | Kronberg |
| 2005/0080460 A1 | 4/2005 | Wang |
| 2005/0085743 A1 | 4/2005 | Hacker et al. |
| 2005/0177061 A1 | 8/2005 | Alanen et al. |
| 2005/0177062 A1 | 8/2005 | Skrabal et al. |
| 2005/0201598 A1 | 9/2005 | Harel |
| 2005/0215918 A1 | 9/2005 | Frantz |
| 2005/0228309 A1 | 10/2005 | Fisher |
| 2005/0251062 A1 | 11/2005 | Choi |
| 2005/0270051 A1 | 12/2005 | Yee et al. |
| 2005/0283091 A1 | 12/2005 | Kink et al. |
| 2006/0025701 A1 | 2/2006 | Kasahara |
| 2006/0041280 A1 | 2/2006 | Stahmann et al. |
| 2006/0052678 A1 | 3/2006 | Drinan |
| 2006/0064029 A1 | 3/2006 | Arad |
| 2006/0135886 A1 | 6/2006 | Lippert et al. |
| 2006/0184060 A1 | 8/2006 | Belalcazar |
| 2006/0200033 A1 | 9/2006 | Keren et al. |
| 2006/0241513 A1 | 10/2006 | Hatlestad et al. |
| 2006/0241719 A1 | 10/2006 | Foster |
| 2006/0247543 A1 | 11/2006 | Cornish |
| 2006/0258952 A1 | 11/2006 | Stahmann et al. |
| 2006/0264776 A1 | 11/2006 | Stahmann et al. |
| 2006/0270942 A1 | 11/2006 | Mcadams |
| 2007/0007975 A1 | 1/2007 | Hawkins |
| 2007/0024310 A1 | 2/2007 | Tokuno et al. |
| 2007/0049993 A1 | 3/2007 | Hofmann et al. |
| 2007/0156061 A1 | 7/2007 | Hess |
| 2007/0188219 A1 | 8/2007 | Segarra |
| 2007/0208233 A1 * | 9/2007 | Kovacs ............... A61B 5/0205  600/300 |
| 2007/0246046 A1 | 10/2007 | Teschner et al. |
| 2007/0270707 A1 | 11/2007 | Belalcazar |
| 2008/0001608 A1 | 1/2008 | Saulnier |
| 2008/0027350 A1 | 1/2008 | Webler |
| 2008/0051643 A1 | 2/2008 | Park et al. |
| 2008/0064981 A1 | 3/2008 | Gregory |
| 2008/0139957 A1 | 6/2008 | Hubbard et al. |
| 2008/0200802 A1 | 8/2008 | Bhavaraju et al. |

(56) References Cited

U.S. PATENT DOCUMENTS

| | | |
|---|---|---|
| 2008/0221475 A1* | 9/2008 | Gregory .............. A61B 5/0536 600/547 |
| 2008/0247502 A1 | 10/2008 | Liao |
| 2008/0252304 A1 | 10/2008 | Woo et al. |
| 2008/0287823 A1 | 11/2008 | Chetham |
| 2008/0306400 A1 | 12/2008 | Takehara |
| 2009/0018432 A1 | 1/2009 | He |
| 2009/0043222 A1 | 2/2009 | Chetham |
| 2009/0069708 A1 | 3/2009 | Hatlestad et al. |
| 2009/0076410 A1 | 3/2009 | Libbus et al. |
| 2009/0082679 A1 | 3/2009 | Chetham |
| 2009/0084674 A1 | 4/2009 | Holzhacker et al. |
| 2009/0093730 A1 | 4/2009 | Grassl |
| 2009/0143663 A1 | 6/2009 | Chetham |
| 2009/0209872 A1 | 8/2009 | Pop |
| 2009/0216140 A1 | 8/2009 | Skrabal |
| 2009/0216148 A1 | 8/2009 | Freed |
| 2009/0234244 A1 | 9/2009 | Tanaka |
| 2009/0240163 A1 | 9/2009 | Webler |
| 2009/0264727 A1 | 10/2009 | Markowitz |
| 2009/0264745 A1 | 10/2009 | Markowitz |
| 2009/0264791 A1 | 10/2009 | Gregory |
| 2009/0275854 A1 | 11/2009 | Zielinski |
| 2009/0275855 A1 | 11/2009 | Zielinski |
| 2009/0326408 A1 | 12/2009 | Moon |
| 2010/0007357 A1 | 1/2010 | Ammari et al. |
| 2010/0049077 A1 | 2/2010 | Sadleir |
| 2010/0056881 A1 | 3/2010 | Libbus et al. |
| 2010/0094160 A1 | 4/2010 | Eror et al. |
| 2010/0100003 A1 | 4/2010 | Chetham et al. |
| 2010/0106046 A1 | 4/2010 | Shochat |
| 2010/0152605 A1 | 6/2010 | Ward |
| 2010/0191141 A1 | 7/2010 | Aberg |
| 2010/0228143 A1 | 9/2010 | Teschner et al. |
| 2011/0034806 A1 | 2/2011 | Hartov et al. |
| 2011/0046505 A1 | 2/2011 | Cornish et al. |
| 2011/0054344 A1 | 3/2011 | Slizynski |
| 2011/0060241 A1 | 3/2011 | Martinsen et al. |
| 2011/0082383 A1 | 4/2011 | Cory et al. |
| 2011/0208084 A1 | 8/2011 | Seoane Martinez |
| 2011/0230784 A2 | 9/2011 | Slizynski |
| 2011/0245712 A1 | 10/2011 | Patterson |
| 2011/0274327 A1 | 11/2011 | Wehnes et al. |
| 2011/0282180 A1 | 11/2011 | Goldkuhl et al. |
| 2012/0071772 A1 | 3/2012 | Chetham |
| 2012/0165884 A1 | 6/2012 | Xi |
| 2012/0238896 A1 | 9/2012 | Garber et al. |
| 2013/0102873 A1 | 4/2013 | Hamaguchi |
| 2013/0165760 A1 | 6/2013 | Erlinger et al. |
| 2013/0165761 A1 | 6/2013 | De Limon et al. |
| 2014/0148721 A1 | 5/2014 | Erlinger |
| 2014/0371566 A1 | 12/2014 | Raymond et al. |

FOREIGN PATENT DOCUMENTS

| | | |
|---|---|---|
| EP | 0 865 763 A2 | 9/1998 |
| EP | 1 078 597 A2 | 2/2001 |
| EP | 1 080 686 A1 | 3/2001 |
| EP | 1 112 715 A1 | 7/2001 |
| EP | 1 118 308 A1 | 7/2001 |
| EP | 1 247 487 A1 | 10/2002 |
| EP | 1 329 190 A1 | 7/2003 |
| EP | 1 353 595 B1 | 8/2008 |
| WO | 91/19454 A1 | 12/1991 |
| WO | 93/18821 A1 | 9/1993 |
| WO | 94/10922 A1 | 5/1994 |
| WO | 96/01586 A1 | 1/1996 |
| WO | 97/11638 A2 | 4/1997 |
| WO | 97/24156 A1 | 7/1997 |
| WO | 98/06328 A1 | 2/1998 |
| WO | 98/33553 A1 | 8/1998 |
| WO | 98151211 A1 | 11/1998 |
| WO | 99/42034 A2 | 8/1999 |
| WO | 99/48422 A1 | 9/1999 |
| WO | 00/19886 A1 | 4/2000 |
| WO | 00/78213 A2 | 12/2000 |
| WO | 01/27605 A1 | 4/2001 |
| WO | 01/52733 A1 | 7/2001 |
| WO | 02/053028 A2 | 7/2002 |
| WO | 2004/021880 A1 | 3/2004 |
| WO | 2004/030535 A1 | 4/2004 |
| WO | 2004/047638 A1 | 6/2004 |
| WO | 2004/084087 A1 | 9/2004 |
| WO | 2004/084723 A1 | 10/2004 |
| WO | 2005/051163 A2 | 6/2005 |
| WO | 2005/122881 A1 | 12/2005 |
| WO | 2006/045051 A1 | 4/2006 |
| WO | 2006/056074 A1 | 6/2006 |
| WO | 2007/070997 A1 | 6/2007 |
| WO | 2007/128952 A1 | 11/2007 |
| WO | 2008/011716 A1 | 1/2008 |
| WO | 2009/027812 A2 | 3/2009 |
| WO | 2009/068961 A2 | 6/2009 |
| WO | 2009/112965 A1 | 9/2009 |
| WO | 2010/003162 A1 | 1/2010 |
| WO | 2010/029465 A2 | 3/2010 |
| WO | 2010/069023 A2 | 6/2010 |
| WO | 2010/076719 A1 | 7/2010 |
| WO | 2011/018744 A1 | 2/2011 |
| WO | 2011/113169 A1 | 9/2011 |
| WO | 2011/136867 A1 | 11/2011 |
| WO | 2014/176420 A1 | 10/2014 |

OTHER PUBLICATIONS

English Translation of CN12336597 published Dec. 1, 1999.
English Translation of CN1329875A published Jan. 9, 2002.
English Translation of JP2001037735 published Feb. 13, 2001.
English Translation of JP2001061804 published Mar. 13, 2001.
English Translation of JP2002502274 published Jan. 22, 2002.
English Translation of JP2003502092 published Jan. 21, 2003.
English Translation of JP2006501892 published Jan. 19, 2006.
English Translation of JP2008502382 published Jan. 31, 2008.
English Translation of JP2010526604 published Aug. 5, 2010.
English Abstract for WO9948422 published Sep. 30, 1999.
English Abstract for WO0152733 published Jul. 26, 2001.
Bernstein, "A new stroke volume equation for thoracic electrical bioimpedance: Theory and rationale," Critical Care Medicine, 1986, pp. 904-909, vol. 14, No. 10.
Blad and Baldetorp, "Impedance spectra of tumour tissue in comparison with normal tissue; a possible clinical application for electrical impedance tomography," Physiol. Meas., 1996, pp. A105-A115, vol. 17.
Lorenzo et al., "Determination of Intracelliar Water by Multifrequency Bioelectrical Impedance," Ann. Nutr. Metab., 1995, pp. 177-184, vol. 39.
Edwards, "A Modified Pseudosection for Resistivity and IP," Geophysics, Aug. 1977, pp. 1020-1036, vol. 42, No. 5.
Hansen, "On the influence of shape and variations in conductivity of the sample on four-point measurements," Appl. Sci. Res., 1959, pp. 93-104, Section B, vol. 8.
Igel, "On the Small-Scale Variability of Electrical Soil Properties and its Influence on Geophysical Measurements," Dissertation, University of Frankfurt, 2007, pp. 1-188.
Kyle et al., "Bioelectrical impedance analysis—part I: review of principals and methods," Clinical Nutrition, 2004, pp. 1226-1243, vol. 23.
Loke and Barker, "Least-squares deconvolution of apparent resistivity pseudosections," Geophysics, Nov. Dec. 1995, pp. 1682-1690, vol. 60, No. 6.
McAdams and Jossinet, "Tissue impedance: a historical overview," Physiol. Meas., 1995, pp. A1-A13, vol. 16.
McEwan and Holder, "Battery powered and wireless Electrical Impedance Tomography Spectroscopy Imaging using Bluetooth," IFMBE Proceedings, 2007, pp. 798-801, vol. 16.
Roy and Apparao, "Depth of investigation in direct current methods," Geophysics, Oct. 1971, pp. 943-959, vol. 36, No. 5.

(56) References Cited

OTHER PUBLICATIONS

Wilson et al., "Feasibility studies of electrical impedance spectroscopy for monitoring tissue response to photodynamic therapy," SPIE, May 1998, pp. 69-80, vol. 3247.

* cited by examiner

Fig. 6A
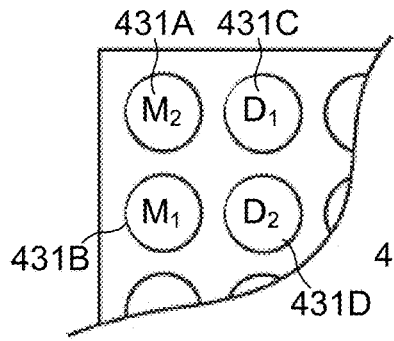
Fig. 6B
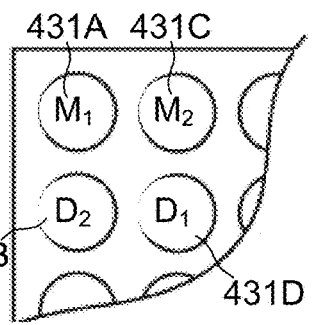
Fig. 6C
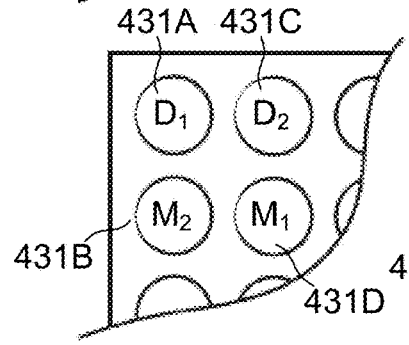
Fig. 6D
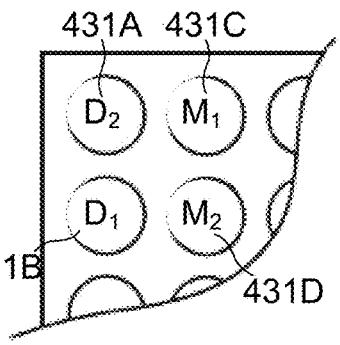
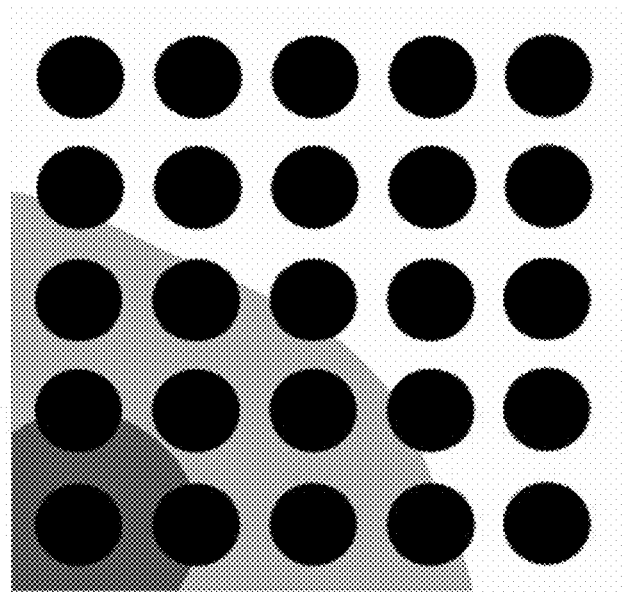
Fig. 7

IMPEDANCE MEASUREMENT PROCESS

BACKGROUND OF THE INVENTION

The present invention relates to a method and apparatus for performing impedance measurements, and in particular to performing multiple impedance measurements at a given site to determine the presence, absence or degree of biological anomalies such as tissue lesions, and to allow impedance mapping to be performed accounting for any erroneous measurements.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

One existing technique for determining biological parameters relating to a subject, such as fluid levels, involves the use of bioelectrical impedance. This involves measuring the electrical impedance of a subject's body using a series of electrodes placed on the skin surface. Changes in electrical impedance at the body's surface are used to determine parameters, such as changes in fluid levels, associated with the cardiac cycle or oedema, or other conditions which affect body habitus.

However, a number of factors, such as the connectively of the electrodes to the subject, can effect the accuracy of impedance measuring processes. An example of this is encountered with tetrapolar electrode configurations, which are routinely used for tissue characterisation. The tetrapolar configuration involves injecting a constant drive current between an adjacent pair of electrodes (drive electrodes), and measurement of the resulting potential between another pair of adjacent electrodes (measurement electrodes). This measured potential is dependent on the electrical characteristics of the volume of tissues being analysed. However, the tetrapolar configuration can produce erroneous results in the form of an increase in measured impedance when a low impedance lesion is located between a drive and measurement electrode.

As a result, when readings are obtained, it can be difficult to determine if the readings are accurate and if not, to determine the cause of the inaccuracy.

SUMMARY OF THE PRESENT INVENTION

The present invention seeks to substantially overcome, or at least ameliorate, one or more disadvantages of existing arrangements.

In a first broad form the present invention seeks to provide a method for use in performing impedance measurements on a subject, the method including, in a processing system:
  a) determining at least one first impedance value, measured at a site using a first electrode configuration;
  b) determining at least one second impedance value, measured at the site using a second electrode configuration; and,
  c) determining the presence, absence or degree of an anomaly using the first and second impedance values.

Typically the method includes using a tetrapolar electrode arrangement, the first and second electrode configurations using a different configuration of drive and measurement electrodes.

Typically the method includes, in the processing system, determining an impedance value for each of four electrode configurations.

Typically the method uses apparatus including a signal generator, a sensor, a switching device and an electrode array having a number of electrodes, and wherein the method includes in the processing system, controlling the electrode configuration by:
  a) selectively interconnecting the signal generator and electrodes using the switching device; and,
  b) selectively interconnecting the sensor and electrodes using the switching device.

Typically the method includes, in the processing system:
  a) causing at least one drive signals to be applied to the subject;
  b) measuring at least one induced signal across the subject; and,
  c) determining at least one impedance value using an indication of the excitation signal and the induced signal.

Typically the method includes, in the processing system:
  a) determining impedance values at a number of different sites; and,
  b) determining an impedance map using the impedance values at each site.

Typically the method includes, in the processing system:
  a) determining the presence of an anomaly at any one of the sites; and,
  b) determining the impedance map taking the anomaly into account.

Typically the method includes, in the processing system, for a site having an anomaly, at least one of:
  a) excluding the site from the impedance map;
  b) modifying the impedance value determined for the site.

Typically the method includes, in the processing system:
  a) determining a difference between the first and second impedance values; and,
  b) determining the presence, absence or degree of an anomaly using the determined difference.

Typically the method includes, in the processing system:
  a) determining a difference between the first and second impedance values;
  b) comparing the difference to a reference; and,
  c) determining an anomaly depending on the result of the comparison.

Typically the method includes, in the processing system:
  a) comparing first and second impedance values; and,
  b) determining the presence, absence or degree of a biological anomaly using the results of the comparison.

Typically the reference in a previously measured difference value for the subject.

Typically the impedance values are at least one of:
  a) measured impedance values; and,
  b) impedance parameter values derived from measured impedance values.

Typically the impedance parameter values include at least one of:
  a) an impedance at infinite applied frequency ($R_\infty$);
  b) an impedance at zero applied frequency ($R_0$); and,
  c) an impedance at a characteristic frequency ($Z_c$).

Typically the method includes, in the processing system, determining the impedance parameter values at least in part using the equation:

$$Z = R_\infty + \frac{R_0 - R_\infty}{1 + (j\omega\tau)^{(1-\alpha)}}$$

where: $R_\infty$=impedance at infinite applied frequency;
  $R_0$=impedance at zero applied frequency;
  $\omega$=angular frequency;

τ is the time constant of a capacitive circuit modelling the subject response; and, α has a value between 0 and 1.

Typically the method includes, in the processing system:
a) causing at least one first impedance value to be measured at a site using a first electrode configuration; and,
b) causing at least one second impedance value to be measured at the site using a second electrode configuration.

Typically the processing system forms part of a measuring device for performing impedance measurements.

Typically the anomaly includes any one or a combination of:
a) a tissue anomaly; and,
b) an erroneous measurement.

Typically the tissue anomaly is a tissue lesion.

Typically the impedance measurements are performed using apparatus including an electrode array having a number of electrodes provided thereon, and wherein the method includes, in the processing system, causing impedance measurements to be performed using different ones of the electrodes in the array.

Typically the method includes:
a) causing a first measurement to be performed at a site using first and second electrodes as drive electrodes and using third and fourth electrodes as measurement electrodes; and,
b) causing a second measurement to be performed at the site using first and third electrodes as drive electrodes and using second and fourth electrodes as measurement electrodes.

Typically the method includes:
a) causing a measurement to be performed at a site using first and second electrodes as drive electrodes and using third and fourth electrodes as measurement electrodes; and,
b) causing a measurement to be performed at a second site using at least two of the first, second, third and fourth electrodes.

Typically the method includes:
a) causing a first measurement to be performed at a first site using first and second electrodes as drive electrodes and using third and fourth electrodes as measurement electrodes;
b) causing a second measurement to be performed at the first site using first and third electrodes as drive electrodes and using second and fourth electrodes as measurement electrodes.
c) causing a first measurement to be performed at a second site using third and fifth electrodes as drive electrodes and using fourth and sixth electrodes as measurement electrodes; and,
d) causing a second measurement to be performed at the second site using third and fourth electrodes as drive electrodes and using fifth and sixth electrodes as measurement electrodes.

Typically the apparatus includes a signal generator for generating drive signals, a sensor for sensing measured signals, and a multiplexer, and wherein the method includes, in the processing system selectively interconnecting the signal generator and the sensor to electrodes in the array using the multiplexer.

In a second broad form the present invention seeks to provide apparatus for use in analysing impedance measurements performed on a subject, the apparatus including a processing system for:

a) determining at least one first impedance value, measured at a site using a first electrode configuration;
b) determining at least one second impedance value, measured at the site using a second electrode configuration; and,
c) determining the presence, absence or degree of an anomaly using the first and second impedance values.

Typically the apparatus includes:
a) a signal generator for applying drive signals to the subject using drive electrodes; and,
b) a sensor for determining measured signals using measurement electrodes.

Typically the processing system is for:
a) causing the signal generator to apply one or more drive signals to the subject; and,
b) determining an indication of the measured signals measured using the sensor.

Typically the processing system is for:
a) determining an indication of drive signals applied to the subject;
b) determining an indication of measured signals determined using the sensor; and,
c) using the indications to determine an impedance.

Typically the apparatus includes an electrode array having a number of electrodes provided thereon, and wherein in use, selected ones of the electrodes are used as drive and measurement electrodes.

Typically the processing system is for:
a) causing a first measurement to be performed at a site using first and second electrodes as drive electrodes and using third and fourth electrodes as measurement electrodes; and,
b) causing a second measurement to be performed at the site using first and third electrodes as drive electrodes and using second and fourth electrodes as measurement electrodes.

Typically the method includes:
a) causing a measurement to be performed at a site using first and second electrodes as drive electrodes and using third and fourth electrodes as measurement electrodes; and,
b) causing a measurement to be performed at a second site using at least two of the first, second, third and fourth electrodes.

Typically the method includes:
a) causing a first measurement to be performed at a first site using first and second electrodes as drive electrodes and using third and fourth electrodes as measurement electrodes;
b) causing a second measurement to be performed at the first site using first and third electrodes as drive electrodes and using second and fourth electrodes as measurement electrodes.
c) causing a first measurement to be performed at a second site using third and fifth electrodes as drive electrodes and using fourth and sixth electrodes as measurement electrodes; and,
d) causing a second measurement to be performed at the second site using third and fourth electrodes as drive electrodes and using fifth and sixth electrodes as measurement electrodes.

Typically the apparatus includes:
a) a signal generator for generating drive signals;
b) a sensor for sensing measured signals; and,
c) a multiplexer, and wherein the processing system is for selectively interconnecting the signal generator and the sensor to electrodes in the array using the multiplexer.

In a third broad form the present invention seeks to provide a method for use diagnosing the presence, absence or degree of a biological anomaly in a subject by using impedance measurements performed on the subject, the method including, in a processing system:

a) determining at least one first impedance value, measured at a site using a first electrode configuration;
b) determining at least one second impedance value, measured at the site using a second electrode configuration; and,
c) determining the presence, absence or degree of an anomaly using the first and second impedance values.

It will be appreciated that the broad forms of the invention may be used individually or in combination, and may be used for diagnosis of the presence, absence or degree of a range of conditions and illnesses, including, but not limited to the detection of lesions, tumours, or the like, as well as to allow impedance mapping to be performed more accurately by accounting for erroneous readings.

BRIEF DESCRIPTION OF THE DRAWINGS

An example of the present invention will now be described with reference to the accompanying drawings, in which:—

FIGS. 6A to 6D are schematic diagrams of example tetrapolar electrode configurations;

FIG. 7 is a schematic diagram of an example of a region of red blood cells introduced to a plasma to show visible diffusion;

DETAILED DESCRIPTION OF THE PREFERRED EMBODIMENTS

Figure 1:
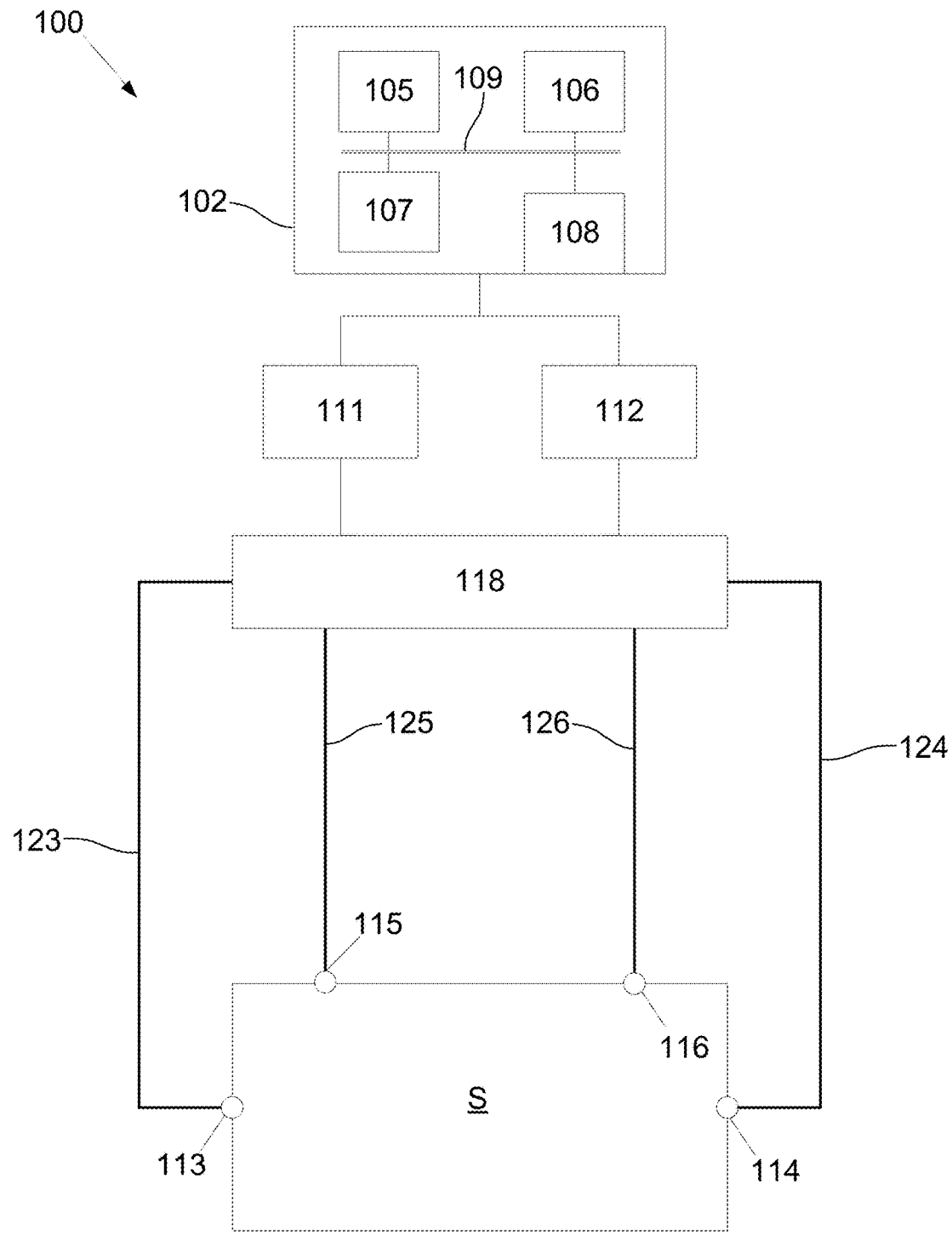
FIG. 1 is a schematic of an example of impedance measuring apparatus.

An example of apparatus suitable for performing an analysis of a subject's bioelectric impedance will now be described with reference to FIG. 1.

As shown the apparatus includes a measuring device 100 including a processing system 102 coupled to a signal generator 111 and a sensor 112. In use the signal generator 111 and the sensor 112 are coupled to first electrodes 113, 114, and second electrodes 115, 116, provided on a subject S, via respective first leads 123, 124, and second leads 125, 126.

The connection may be via a switching device 118, such as a multiplexer, allowing the leads 123, 124, 125, 126 to be selectively interconnected to signal generator 111 and the sensor 112, although this is not essential, and connections may be made directly between the signal generator 111, the sensor 112 and the electrodes 113, 114, 115, 116.

The processing system 102 typically includes a processor 105, a memory 106, an input/output device 107 such as a keyboard and display, and an external interface 108 coupled together via a bus 109, as shown. The external interface 108 can be used to allow the processing system 102 to be coupled to the signal generator 111 and the sensor 112, as well as to allow connection to one or more peripheral devices (not shown), such as an external database, or the like.

In use, the processing system 102 is adapted to generate control signals, which cause the signal generator 111 to generate one or more alternating drive signals, such as voltage or current signals, which can be applied to a subject S, via two of the electrodes 113, 114, 115, 116 (generally referred to as "drive" electrodes). The sensor 112 then determines measured signals representing the induced voltage across or current through the subject S, using the other two of the electrodes 113, 114, 115, 116 (generally referred to as "measurement" electrodes) and transfers appropriate signals to the processing system 102.

Accordingly, it will be appreciated that the processing system 102 may be any form of processing system which is suitable for generating appropriate control signals and interpreting an indication of the measured signals to thereby determine the subject's bioelectrical impedance, and optionally determine other information such as the presence, absence or degree of oedema, or the like.

The processing system 102 may therefore be a suitably programmed computer system, such as a laptop, desktop, PDA, smart phone or the like. Alternatively the processing system 102 may be formed from specialised hardware, such as an FPGA (field programmable gate array), or a combination of a programmed computer system and specialised hardware, or the like.

In use, the two electrodes 113, 114, 115, 116 that are to be used as drive electrodes are positioned on the subject to allow one or more signals to be injected into the subject S, with two other electrodes 113, 114, 115, 116 being positioned to act as measurement electrodes to allow signals induced within the subject, to be detected. The location of the electrodes will depend on the segment of the subject S under study.

Once the electrodes are positioned, one or more alternating signals are applied to the subject S, via the drive electrodes. The nature of the alternating signal will vary depending on the nature of the measuring device and the subsequent analysis being performed.

For example, the system can use Bioimpedance Analysis (BIA) in which a single low frequency current is injected into the subject S, with the measured impedance being used directly in the identification of anomalies (which can include tissue anomalies, erroneous measurements, or the like), or performing impedance mapping.

In contrast Bioimpedance Spectroscopy (BIS) devices apply signals at a number of frequencies either simultaneously or sequentially. BIS devices typically utilise frequencies ranging from low frequencies (4 kHz) to higher frequencies (1000 kHz), and can use 256 or more different frequencies within this range, to allow multiple impedance measurements to be made within this range.

Thus, the measuring device 100 may either apply an alternating signal at a single frequency, at a plurality of frequencies simultaneously, or may apply a number of alternating signals at different frequencies sequentially, depending on the preferred implementation. The frequency or frequency range of the applied signals may also depend on the analysis being performed.

In one example, the applied signal is a frequency rich current signal from a current source clamped, or otherwise limited, so it does not exceed a maximum allowable subject auxiliary current. However, alternatively, voltage signals may be applied, with a current induced in the subject being measured. The signal can either be constant current, impulse function or a constant voltage signal where the current is measured so it does not exceed the maximum allowable subject auxiliary current.

A potential difference and/or current are measured between the measurement electrodes. The acquired signal and the measured signal will be a superposition of potentials generated by the human body, such as the ECG, and potentials generated by the applied current.

To assist accurate measurement of the impedance, buffer circuits may be placed in connectors that are used to connect the electrodes 113, 114, 115, 116 to the leads 123, 124, 125, 126. This helps eliminate contributions to the measured voltage due to the response of the leads 123, 124, 125, 126, and reduce signal losses.

A further option is for the voltage to be measured differentially, meaning that the sensor used to measure the potential at each measurement electrode only needs to measure half of the potential as compared to a single ended system. In one example, current can also be driven or sourced through the subject S differentially, which again greatly reduced the parasitic capacitances by halving the common-mode current.

The acquired signal is demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a processing technique such as multiplying the measured signal with a reference sine wave and cosine wave derived from the signal generator, or with measured sine and cosine waves, and integrating over a whole number of cycles. This process rejects any harmonic responses and significantly reduces random noise.

Other suitable digital and analog demodulation techniques will be known to persons skilled in the field.

In the case of BIS, impedance or admittance measurements can be determined from the signals at each frequency by comparing the recorded voltage and current signal. This allows demodulation to be used to produce an amplitude and phase signal at each frequency.

Figure 2:
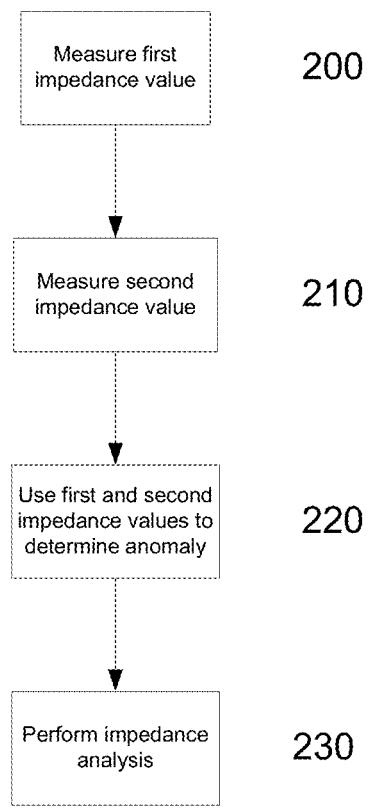
FIG. 2 is a flowchart of an example of a process for performing impedance measurements.

An example of the operation of the apparatus to detect anomalies when performing impedance mapping or other impedance measurements will now be described with reference to FIG. 2.

At step 200 a first impedance value is measured at a given site. The impedance value is typically measured using a first electrode configuration, and whilst any form of electrode configuration may be used, this is typically a tetrapolar electrode configuration utilised to allow impedance readings to be measured at the specific site.

At step 210 a second impedance value is measured at the (same) site. This is typically achieved utilising an alternative electrode configuration and in particular, a configuration which is a modified version of the first configuration.

In this regard, the configuration typically utilises the same electrode placements on the subject, but applies the signals to and measures signals from different ones of the electrodes. Thus, for example, in a tetrapolar electrode configuration, the first measurement may be made by applying a current across first electrodes and measuring a voltage across second electrodes, whereas the second measurement may be made by applying the current across the second electrodes and measuring the induced voltage across first electrodes.

At step 220 the first and second impedance values can be used to determine if the measurement made at the site is erroneous. In particular, such a reading will typically arise if a low impedance lesion or other biological anomaly is present between a drive and a measurement electrode pair.

The erroneous measurement (or reading) can then be taken into account when performing analysis of impedance measurements at step 230. For example, the erroneous reading may be used to identify and/or subsequently monitor the development of a low impedance lesion. Thus, this technique can be used to detect the presence, absence or degree of lesions or other biological anomalies. Additionally, and/or alternatively, knowledge of the anomaly can be taken into account when performing analysis of impedance measurements.

Thus, for example, impedance measurements can be performed over a region, such as an area of a subject's skin, to allow impedance mapping or other similar analysis to be performed. As the presence of erroneous readings can have a negative impact on any such impedance mapping process, identification of these erroneous readings allows readings at the corresponding site to be rejected or otherwise modified so that they do not adversely affect the impedance mapping process.

Figure 3:
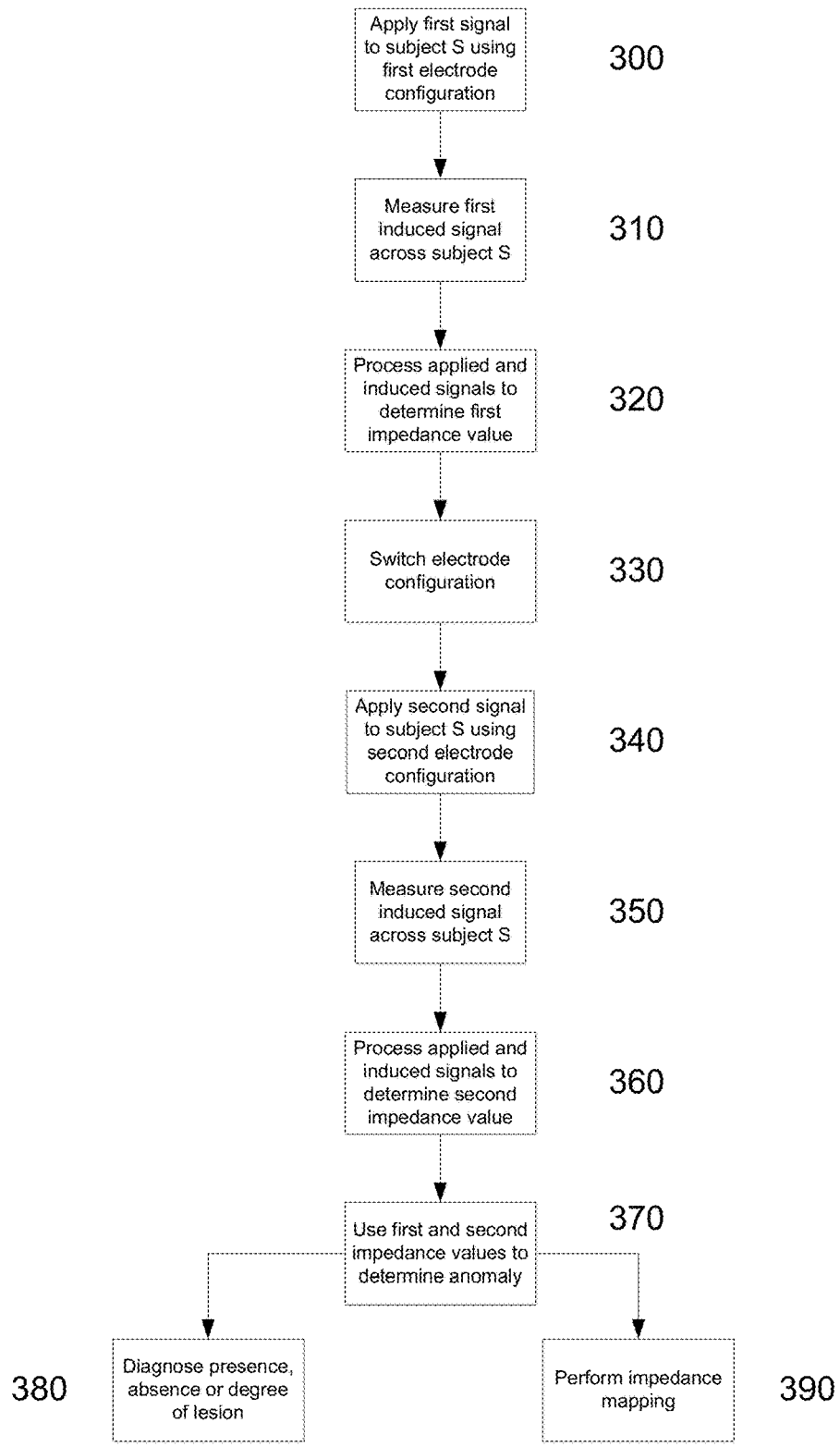
FIG. 3 is a flowchart of a second example of a process for performing impedance measurements.

An example of the process for identifying anomalies, including but not limited to tissue anomalies, erroneous readings, or the like will now be described in more detail with respect to FIG. 3.

In particular, at step 300 the signal generator 111 is used to apply a first drive signal to the subject S using a first electrode configuration. Thus for example, the current source 111 may be connected to the leads 123, 124, via the switching device 118, so that the electrodes 113, 114 act as the drive electrodes.

At step 310 a first signal induced across the subject S is measured. This is typically achieved by utilising the switching device 118 to interconnect the remaining measurement electrodes, in this case the electrodes 115, 116, to the sensor 112, thereby allowing signals induced within the subject S to be detected.

At step 320 the processing system 102 utilises an indication of the applied and induced signals to determine a first impedance value. The first impedance value may be formed from one or more measured impedance values. Thus, for example, if a single frequency BIA device is used, a single measured impedance value may be determined, whereas if a BIS device is used, multiple measured values may be determined, with a single value being determined for each applied frequency.

In addition, or alternatively to the impedance values being actual measured values, the impedance values may be based on impedance parameter values derived from the actual measurements. This can include parameter values such as the impedance at zero, characteristic or infinite frequencies ($R_0$, $Z_c$, $R_\infty$), as will be described in more detail below.

At step 330 the processing system 102 controls the switching device 118 to switch to an alternative electrode configuration. In this instance, for example, the electrodes 113, 115 may be used as the drive electrodes with the electrodes 114, 116 being used as measurement electrodes. Any other alternative configuration may also be used, depending on the implementation.

At step 340, a second signal is applied to the subject S using the second electrode configuration, with the induced signal across subject S being measured at step 350. At step 360 the applied and induced signals are processed to determine a second impedance value, which again can be formed from one or more measured impedance values, or parameter values derived therefrom.

At step 370, the processing system 102 uses the first and second impedance values to determine if any tissue anomalies might exist. An erroneous measurement will typically be determined if the difference between the first and second impedance values is greater than a reference amount. The magnitude of this reference may vary depending upon a number of factors and the processing system 102 is therefore typically arranged to compare the difference between the first and second impedance values to a reference value, which can be stored in memory, or the like. The reference value could be previously determined for example based on sample data collected for a nominal reference population, or based on the difference determined for other sites, as will be described in more detail below.

Once detected, this information can be used in one of two ways. For example, the measured values can be used to derive information regarding any associated biological anomaly, such as the presence, absence or degree of any tissue lesion, tumour, or the like, at step 380. Alternatively, at step 390, the erroneous measurement can be taken into account when performing other impedance analysis. Thus, for example, if wound or other impedance mapping is being performed to monitor wound healing, or the like, any erroneous reading can be rejected to ensure that this does not overtly influence the outcome of the analysis. Examples of this will be described in more detail below.

Figure 4:
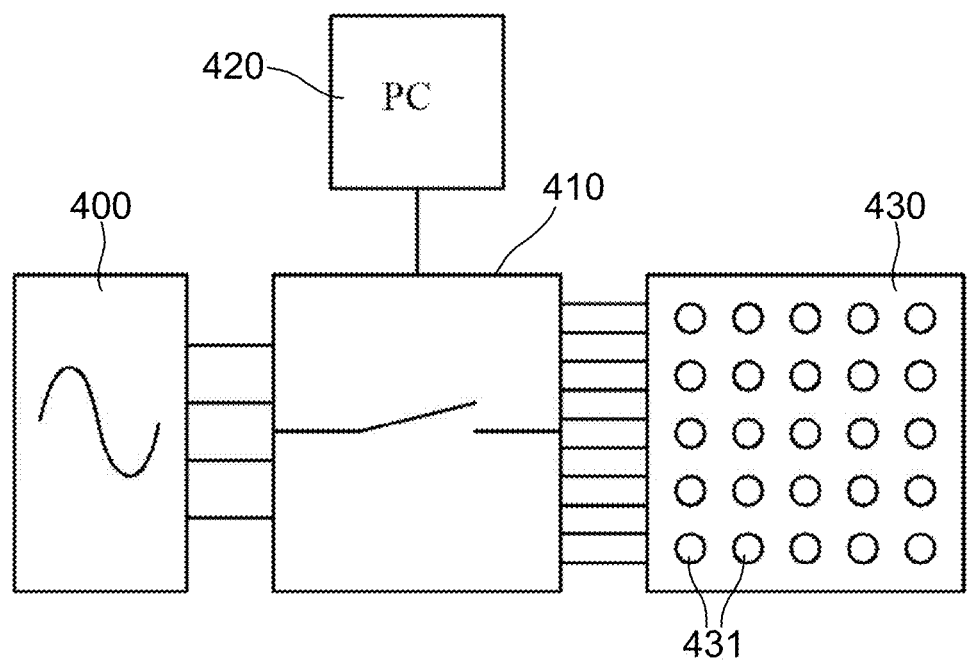
FIG. 4 is a schematic of a specific example of impedance measuring apparatus.

An example of a specific apparatus arrangement for performing impedance measurements, and in particular, for performing impedance mapping, will now be described with reference to FIG. 4.

In particular in this instance an impedance measuring device 400 is connected to a multiplexer 410, which is controlled by a computer system 420, such as a personal computer or the like. In this instance the multiplexer 410 is coupled to an electrode array 430 having a number of electrodes 431 provided thereon.

In use the measuring device 400 generates signals to be applied to the subject via the electrode array with these signals being coupled to respective ones of the electrodes 431 utilising the multiplexer 410. Similarly, signals induced across the subject S can also be returned from electrodes 431 to the impedance measuring device 400 via the multiplexer 410. Overall operation of the multiplexer 410 can be controlled using the computer system 420, allowing this process to be substantially automated.

In one specific example, the measuring device 400 is in the form of an Impedimed Imp SFB7™. The drive and measurement electrodes from the SFB7 can be directed through a multiplexer 410, such as a 32 channel multiplexer (ADG732) from Analog Devices and switching of the multiplexer output channels can be controlled via custom software operating on a standard computer system 420.

In this example, the electrode array 430 includes twenty five, 1 mm diameter electrodes separated by 0.77 mm in a 5×5 square. This allows a total of 64 separate measurements to be taken at 16 different sites giving an impedance map of 49 mm$^2$ on the surface of a subject, which may be an individual, a test medium, or the like. As a result of this, only 25 of the available 32 multiplexer channels are required for this arrangement.

Figure 5A:
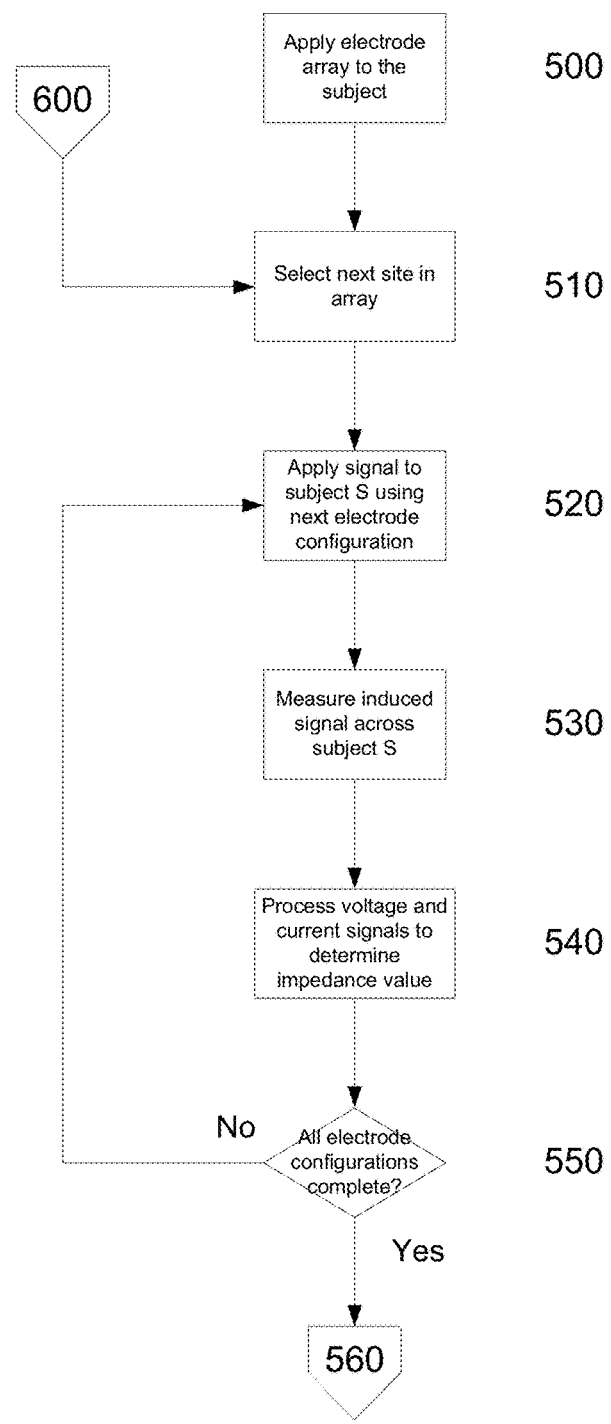
FIGS. 5A and 5B are a flowchart of an example of a process for performing impedance measurements using the apparatus of FIG. 4.
Figure 5B:
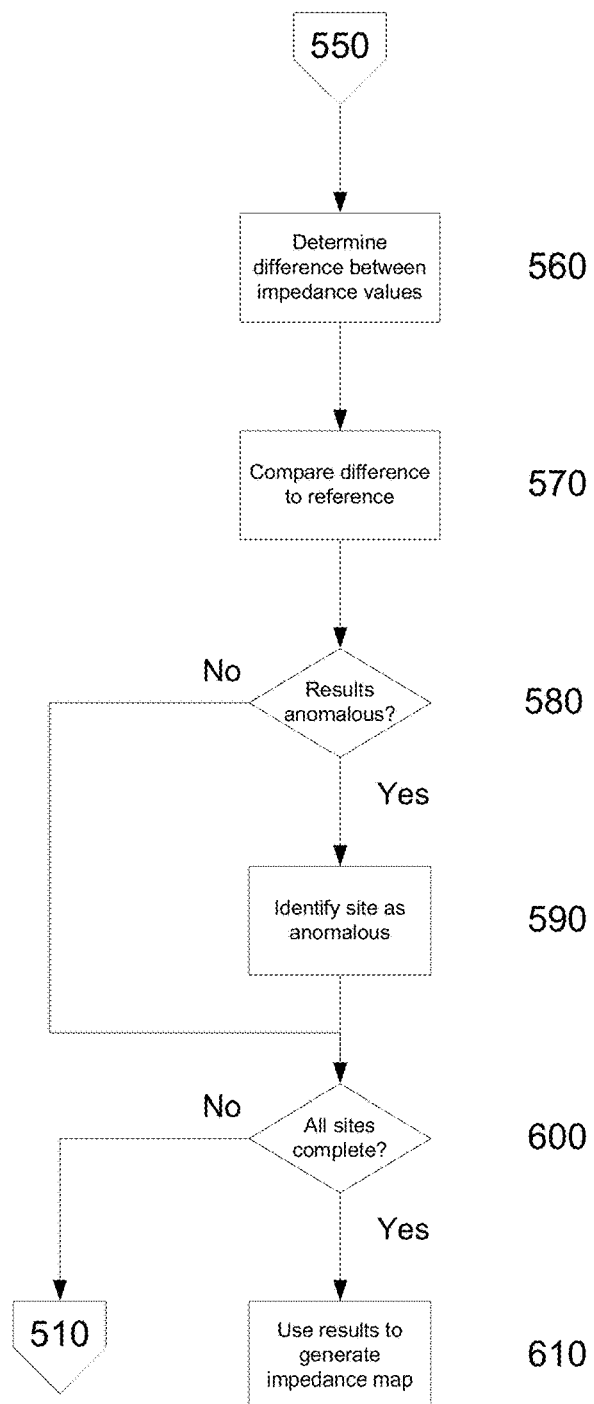
Figure 6E:
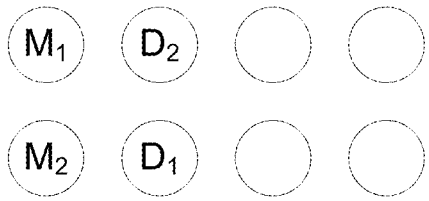
FIGS. 6E to 6J are schematic diagrams of an example of a sequence of electrode configurations used for performing measurements at multiple sites.
Figure 6F:
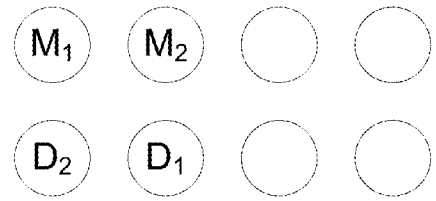
Figure 6G:
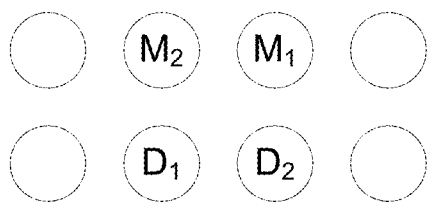
Figure 6H:
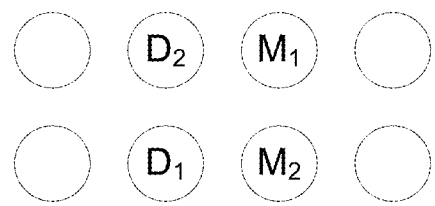
Figure 6I:
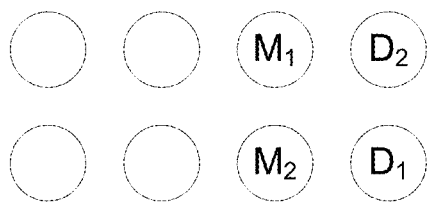
Figure 6J:
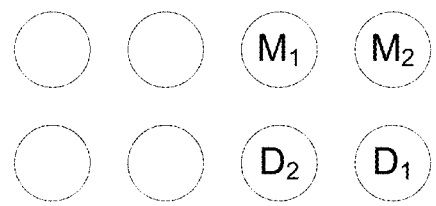

An example of use of the system will now be described with reference to FIG. 5.

At step 500 the electrode array 430 is applied to the subject S, and connected to the multiplexer 410, as described above. At this stage, systems, such as the measuring device 400, the multiplexer 410 and the computer system 420 are activated and configured as required in order to allow the measurement procedure to be performed.

At step 510 the computer system 420 selects a next site for measurement. The electrodes 431 are typically selected so as to form a tetrapolar arrangement, with a group of four electrodes 431 in the array 430 defining the site being measured. An example of this is shown in FIGS. 6A to 6D, in which four electrodes 431A, 431B, 431C, 431D are selectively used as measurement and drive electrodes for a single site.

In this example, four measurements can be made at each site by using the drive and measurement electrode arrangements shown in FIGS. 6A to 6D. Thus, in FIG. 6A, the electrodes 431A, 431B act as the measurement electrodes $M_1$, $M_2$, whereas the electrodes 431C, 431D act as the drive electrodes $D_1$, $D_2$. Successive measurements at the site can be made using different electrode configurations in which the drive and measurement electrodes $M_1$, $M_2$, $D_1$, $D_2$ are used as shown so that the tetrapolar configuration is effectively rotated by 90° for each successive measurement.

To achieve this, at step 520 the measuring device 400 controls the multiplexer 410 to couple the measuring device to the electrodes in accordance with a next one of the electrode configurations for the currently selected tetrapolar array. Thus, for example, for the first measurement, the arrangement shown in FIG. 6A can be used so that the electrodes 431A, 431B act as the measurement electrodes $M_1$, $M_2$, whereas the electrodes 431C, 431D act as the drive electrodes $D_1$, $D_2$.

The measuring device 400 then applies a drive signal to the subject via the selected drive electrodes 431C, 431D, allowing the signal induced across the measurement electrodes 431A, 431B to be measured at step 530. An indication of this measured signal is returned to the measuring device 400, to allow the measuring device 400 to process the voltage and current signals and determine one or more an impedance values.

The impedance values determined will depend on the preferred implementation. For example, in the event that the measuring device 400 is performing BIA, then typically a single impedance value is calculated representing the measured impedance.

In contrast, if the measuring device performs a multiple frequency BIS analysis, as is the case with the SFB7™ device described above, then the impedance value can be based on impedance parameter values, such as values of the impedance at zero, characteristic or infinite frequencies ($R_0$, $Z_c$, $R_\infty$). These values can be derived by the measuring device 400 based on the impedance response of the subject, which at a first level can be modelled using equation (1), commonly referred to as the Cole model:

$$Z = R_\infty + \frac{R_0 - R_\infty}{1 + (j\omega\tau)} \qquad (1)$$

where: $R_\infty$=impedance at infinite applied frequency,
$R_0$=impedance at zero applied frequency,
$\omega$=angular frequency,
$\tau$ is the time constant of a capacitive circuit modelling the subject response.

However, the above represents an idealised situation which does not take into account the fact that the cell membrane is an imperfect capacitor. Taking this into account leads to a modified model in which:

$$Z = R_\infty + \frac{R_0 - R_\infty}{1 + (j\omega\tau)^{(1-\alpha)}} \qquad (2)$$

where: $\alpha$ has a value between 0 and 1 and can be thought of as an indicator of the deviation of a real system from the ideal model.

The value of the impedance parameters $R_0$ and $R_\infty$ may be determined in any one of a number of manners such as by:
 solving simultaneous equations based on the impedance values determined at different frequencies;
 using iterative mathematical techniques;
 extrapolation from a "Wessel plot";
 performing a function fitting technique, such as the use of a polynomial function.

It will be appreciated that as an alternative to the analysis being performed by the measuring device 400, the analysis can be performed in part, or in total, by the computer system 420, depending on the preferred implementation.

At step 550, the processing system 420 determines if all electrode configurations for the respective site are complete and if not returns to step 520. In this instance a next electrode configuration is selected, with steps 520 to 550 being repeated for this next electrode configuration. This process can then be repeated until each of the four electrode configurations shown in FIGS. 6A to 6D have been utilised for the current site.

Whilst it is possible to use all four of the indicated electrode configurations for the tetrapolar configuration, this is not essential, and in some circumstances, it is sufficient to use any two or more of the possible configurations. Thus, for example, the configurations used in FIGS. 6A and 6B can be used, in which the tetrapolar electrode configuration is effectively rotated by 90°. This is particularly useful as one drive and measurement electrode is effectively exchanged in the two different configurations, thereby maximising the chance of lesions located between the drive and measurement electrodes from being located, without requiring switching of each of the electrodes.

Furthermore, this arrangement can be used to provide a sequence of drive and measurement electrode configurations that can be used to perform multiple measurements at successive sites, with only a single drive and single measurement electrode being switched between successive measurements. An example of this is shown in FIGS. 6E to 6J.

Once all the electrode configurations are complete for a specific site, the measuring device 400 or the computer system 420 is used to analyse the impedance values and determine if the impedance measurements are indicative of a tissue anomaly. As mentioned above this may be achieved in any one of a number of ways but typically involves examining the difference between measured impedance values. The reason for this is that the impedance measured at a given site should be substantially invariant irrespective of the electrode configuration used. Consequently, any variation in measured impedance values for different electrode configurations indicates that the tissue is non-uniform and in particular that there is likely to be a low impedance lesion situated between the drive electrodes $D_1$, $D_2$ and the measurement electrodes $M_1$, $M_2$.

In this regard, when the electrodes are provided in the arrangement of FIGS. 6A to 6D, there are usually regions of positive sensitivity between the drive electrodes $D_1$, $D_2$ and between the measurement electrodes $M_1$, $M_2$. In addition to this, there are generally regions of negative sensitivity between each pair of drive and measurement electrodes $D_1$, $M_2$ and $M_1$, $D_2$. These size and magnitude of the areas of negative and positive sensitivity will vary depending on the exact electrode configuration.

For negative field region, a lower resistance than the surrounding tissue will result in an increase in measured impedance, whereas a lower resistance in the positive field region will result in a decrease in measured impedance. Example tissue electrical properties as given by Brown, B. H., Tidy, J. A., Boston, K., Blackett, A. D., Smallwood, R. H. and Sharp, F. (2000a). "*Relation between tissue structure and imposed electrical current flow in cervical neoplasia*," The Lancet 355: 892-895, are shown in Table 1 below.

TABLE 1

| Healthy Tissue Mean (SD) | Cancerous Tissue Mean (SD) |
| --- | --- |
| $R_E$ = 19.0 (7.77) m | $R_E$ = 3.85 (2.89) m |
| $R_I$ = 2.31 (4.04) m | $R_I$ = 6.10 (2.57) m |
| C = 1.12 (1.96) μF/m | C = 1.01 (1.93) μF/m |

Thus, as cancerous tissue generally has a lower resistance, a cancerous lesion between the drive electrodes $D_1$, $D_2$ or between the measurement electrodes $M_1$, $M_2$. will result in a decreased impedance measurement, whereas a lesion between the each pair of drive and measurement electrodes $D_1$, $M_2$ or $M_1$, $D_2$, will result in an increased impedance measurement.

It will therefore be appreciated that examining differences between impedance measurements with different electrode configurations can allow tissue anomalies such as lesions, to be detected.

In one example this is achieved by determining the difference between the impedance values determined using the different electrode configurations, at step 560. The maximum determined difference is then compared to a reference at step 570. The reference, which is typically previously determined and stored in memory of the measuring device 400 or the computer system 420, represents a threshold value so that if the difference between impedance values is greater than the reference, then this indicates that a tissue anomaly is present.

The reference can be determined in any one of a number of ways depending on the preferred implementation. For example, the reference may be determined by studying a number of healthy individuals (individuals without lesions or other biological anomalies) and/or unhealthy individuals (individuals with lesions or other anomalies) and calculating a range of variations between impedance values at a given site. This can be used to provide an indication of typical differences between impedance values for a healthy individual, thereby allowing a threshold to be established for tissue anomalies.

A further alternative is to derive the reference from previous measurements made for the respective individual. For example, if the individual undergoes a medical intervention, such as surgery, or the like, which may result in a lesion forming, then measurements can be made for the individual prior to the intervention, or following initial development of the lesion. This can be used to establish a baseline of differences in impedance values for the individual, either prior to the lesion forming, or following lesion formation. This baseline can then be used as a subject specific reference so that changes in the difference between the impedance values for the individual, can be used to monitor lesion development and/or effectiveness of treatment.

A further option is to determine the reference using a statistical analysis of measurements made for a number of different sites. This could be performed by examining the mean difference for a number of sites over a region, and then calculating the reference based on a value that is a number of standard deviations from the mean. Accordingly, in this instance, an anomaly is identified if the difference for a site is more than a set number of standard deviations from the mean difference value for a number of sites.

In any event, if the reference is exceeded and the result is determined to be indicative of a tissue anomaly at step 580, then the site is identified as a tissue anomaly at step 590. Once this is completed or otherwise, at step 600 the computer system 420 will determine if all sites are complete and if not will return to step 510 to select the next site in the electrode array 430. This will typically involve using the electrodes 631C, 631D and two electrodes in the next column in the array.

This process can be repeated for all of the sites defined by the electrode array 630, allowing an impedance map to be generated at 610. The impedance map can be used to indicate variations in tissue properties, or the like, which in turn can be used for a number of purposes, such as to monitor healing of wounds or the like.

As will be appreciated by persons skilled in the art, being able to identify, and subsequently discount or otherwise account for such tissue anomalies allows improved results to be obtained for impedance mapping processes.

Furthermore, this process can also be used to identify and monitor low impedance lesions, tumours or the like. For example, determining the magnitude of the difference between different impedance values obtained for a given site allows an indication of the severity of the lesion to be determined. By monitoring changes in the difference over time, this allows variations in lesion severity over time to be monitored.

Specific example trials of the process of performing impedance mapping will now be described.

The blood for each trial was collected from the same animal and treated with 70 mg/L of heparin to prevent coagulation. Blood for each measurement was prepared in the same manner by allowing it to cool to room temperature (22° C.) and the red blood cells separated via a centrifuge. The separated red blood cells and plasma could then be mixed in appropriate proportions to obtain the required haematocrit for testing. Samples were also collected and allowed to coagulate, these were used to represent a high impedance tissue medium at $R_0$ due to the small extracellular space.

In a first example, impedance maps were initially established for homogenous haematocrit in an in-vitro environment. To achieve this, bovine blood was used as the conductive medium, with impedance maps being obtained using homogenous samples with a range of haematocrit values (0, 20, 40, 60, 80%).

Figure 8:
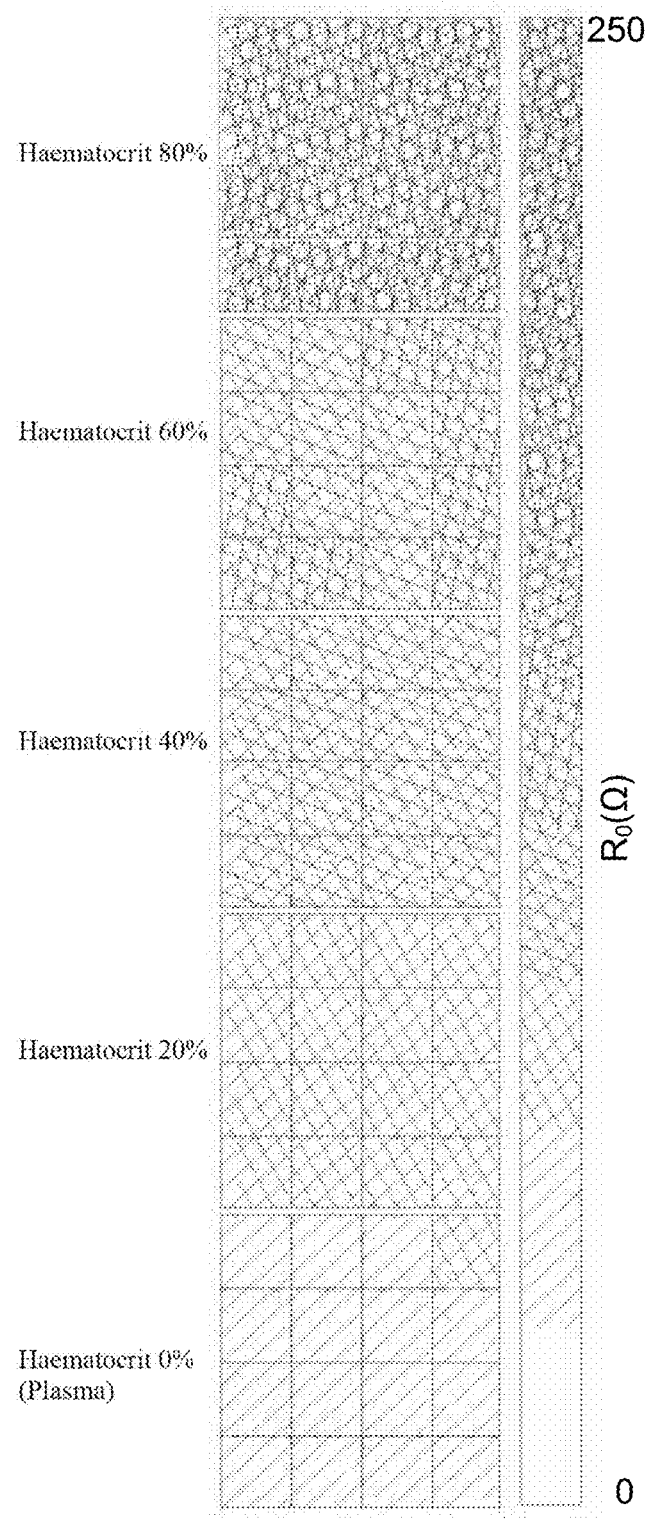
FIG. 8 is a schematic diagram of varying haematocrit value over an area of the electrode array of FIG. 4.
Figure 9A:
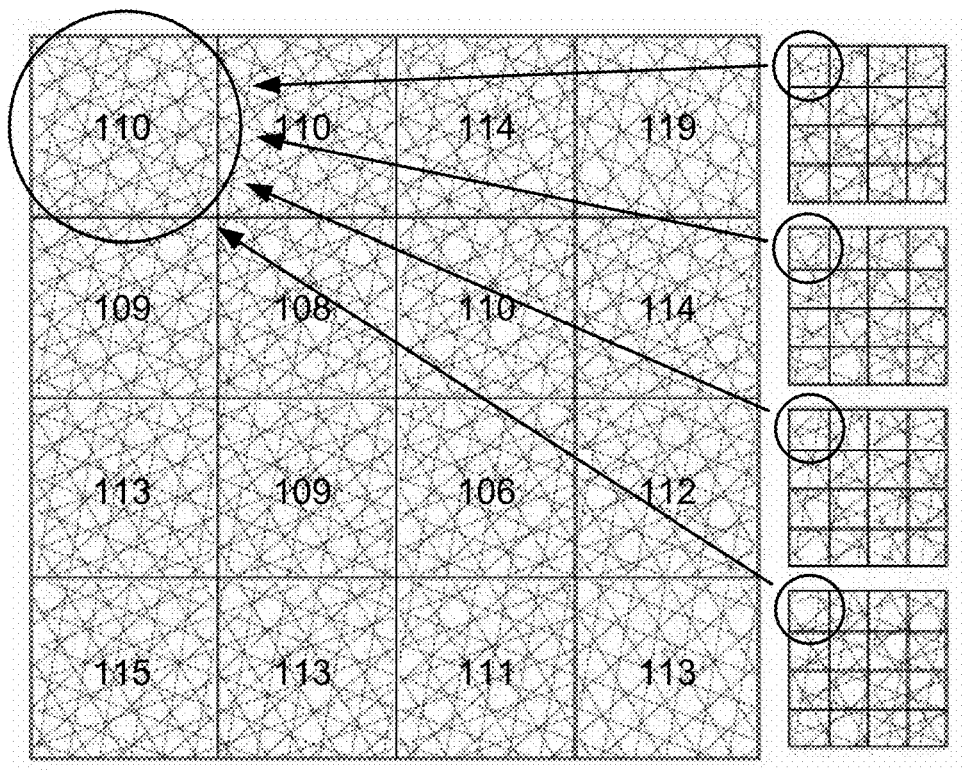
FIG. 9A is a schematic diagram of average $R_0$ maps for haematocrit of 60% and for the tetrapolar electrode arrangements of FIGS. 6A to 6D.

The impedance maps of $R_0$ measured for blood samples of various haematocrit are shown in FIG. 8. Each measurement location shown was measured using the tetrapolar electrode orientation arrangement described above, at each of the four possible electrode orientations. These four $R_0$ values measured using different electrode orientation were then averaged to produce one $R_0$ map as shown in FIG. 9A.

Figure 9B:
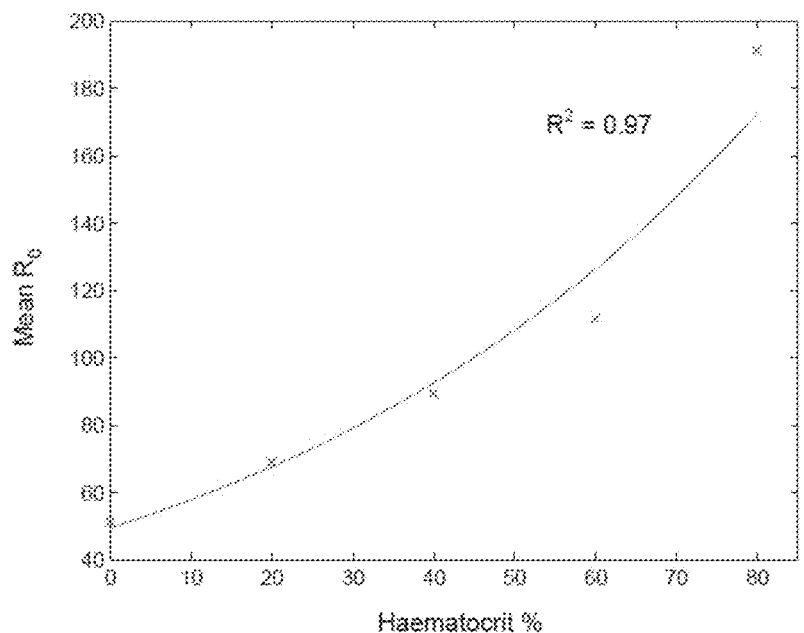
FIG. 9B is a plot of an example of a mean value of $R_0$ for each impedance map of FIG. 9A against haematocrit concentration.

A plot of mean $R_0$ for each impedance map against haematocrit is shown in FIG. 9B. This highlights that there is a large increase in impedance with haematocrit concentration. The plot follows an exponential trend as expected since the $R_0$ value of a sample with haematocrit of 100% would approach infinity due to the very small extracellular space. The range of haematocrit values has also shown to have a significant and measurable change in $R_0$. This is useful if impedance maps were to be determined with two or more volumes of blood with differing haematocrits.

In a second trial, the electrode array 430 was covered with plasma (haematocrit of 0%) and red blood cells (haematocrit of 100%) injected onto the corner of the electrode array, as shown for example in FIG. 7.

Figure 10:
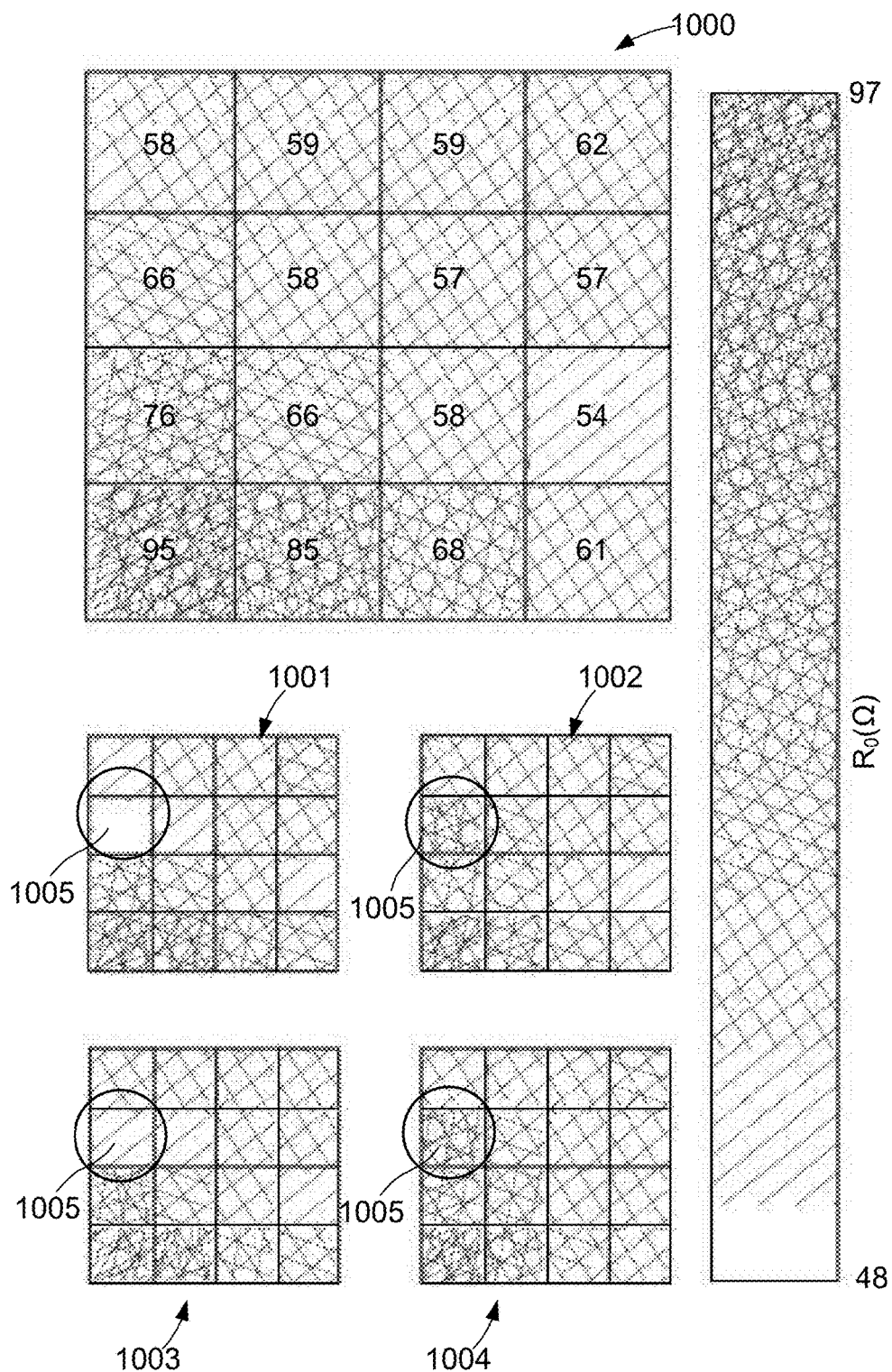
FIG. 10 is a schematic diagram of example impedance maps for plasma with introduced red blood cells in the lower left corner for the tetrapolar electrode arrangements of FIGS. 6A to 6D.

An example of the bioimpedance map of an average value of $R_0$ obtained for each site is shown at 1000 in FIG. 10. The smaller four maps 1001, 1002, 1003, 1004, correspond to the impedance values for $R_0$ measured using respective electrode configurations, as shown for example in FIGS. 6A to 6D.

It is evident from the above examples that bioimpedance maps for haematocrit 0 to 80% result in reasonably consistent values of $R_0$ (standard deviation <3%). The uniform measurements also demonstrate that the remaining 21 electrodes have little effect on the measurements from the 4 electrodes actively involved. Hence these 21 electrodes do not shunt the current between the active drive electrodes.

The bioimpedance map of plasma with introduced cells clearly shows an increase in $R_0$ at the site of the introduced cells, shown in FIG. 10. The $R_0$ value in the lower left corner (95Ω) is much higher than that in the upper right corner (62Ω) which corresponds to that of the homogenous plasma sample. While the resistance in the lower left corner is higher than that of plasma it is less than that obtain for 80 and 60% haematocrit. The reason for this is due to the cells dispersing throughout the plasma (as shown in FIG. 7) effectively reducing the haematocrit of the introduced red blood cell sample.

As shown in this example, the values of $R_0$ determined for the site 1005 differ significantly for the four different orientations, thereby indicating the presence of a biological anomaly at the site 1005.

In this example, the sensitivity region between the two electrodes 431B, 431D is positive for the maps 1002, 1004 resulting in an increased measured impedance if a higher impedance medium is present between the electrodes. This increase in impedance is clearly seen in the maps 1002, 1004. The maps 1001, 1003 on the left show a decrease in impedance because the region between the two electrodes 431B, 431D is of negative sensitivity in this configuration, thereby resulting in a decreased measured impedance when a higher impedance medium is located in the region.

When performing an impedance analysis, the can be taken into account by excluding this site from the larger impedance map, allowing an accurate average to be determined that excludes any anomaly. Alternatively different mechanisms may be used for taking this into account. For example, averaging of the four measured values of $R_0$, at the given site, can reduce the impact of the tissue anomaly. In this regard, the averaged impedance map would be unaffected since the higher and lower measured impedance values effectively average to cancel each other out, so that the $R_0$ value in this region of the larger map is not anomalous.

Alternatively, the impedance of adjacent sites can be used to determine a value for $R_0$ which is unaffected by the tissue anomaly. Thus, for example, examination of the maps 1001, 1002, 1003, 1004 for each tetrapolar configuration highlights that the determined impedance values determined for the site 1005 in the maps 1001, 1003 are similar to those of adjacent sites, whereas the impedance values determined for the site 1005 in the maps 1002, 1004 are significantly different. This implies that the lesion or other tissue anomaly is located between the drive and measurement electrodes for the electrode configurations used in determining the maps 1002, 1004, meaning that these readings are erroneous. Consequently, the impedance value used for the overall impedance map could be based on the impedance values determined for the impedance maps 1001, 1003 as these readings are more likely to be accurate.

This can be performed for example to discount readings that are believed to be anomalous, for example due to errors in the measuring process, poor electrode contact, or the like.

However, more typically the results are used to detect tissue anomalies, such as lesions or the like. Thus, as measurements made using orthogonal electrode orientations at a region of non-homogeneity will produce different measured impedances, whereas a region of homogeneity will produce the same measurements. This allows tissue anomalies, such as lesions, to be identified, and furthermore allows lesion boundaries to be determined.

Figure 11:
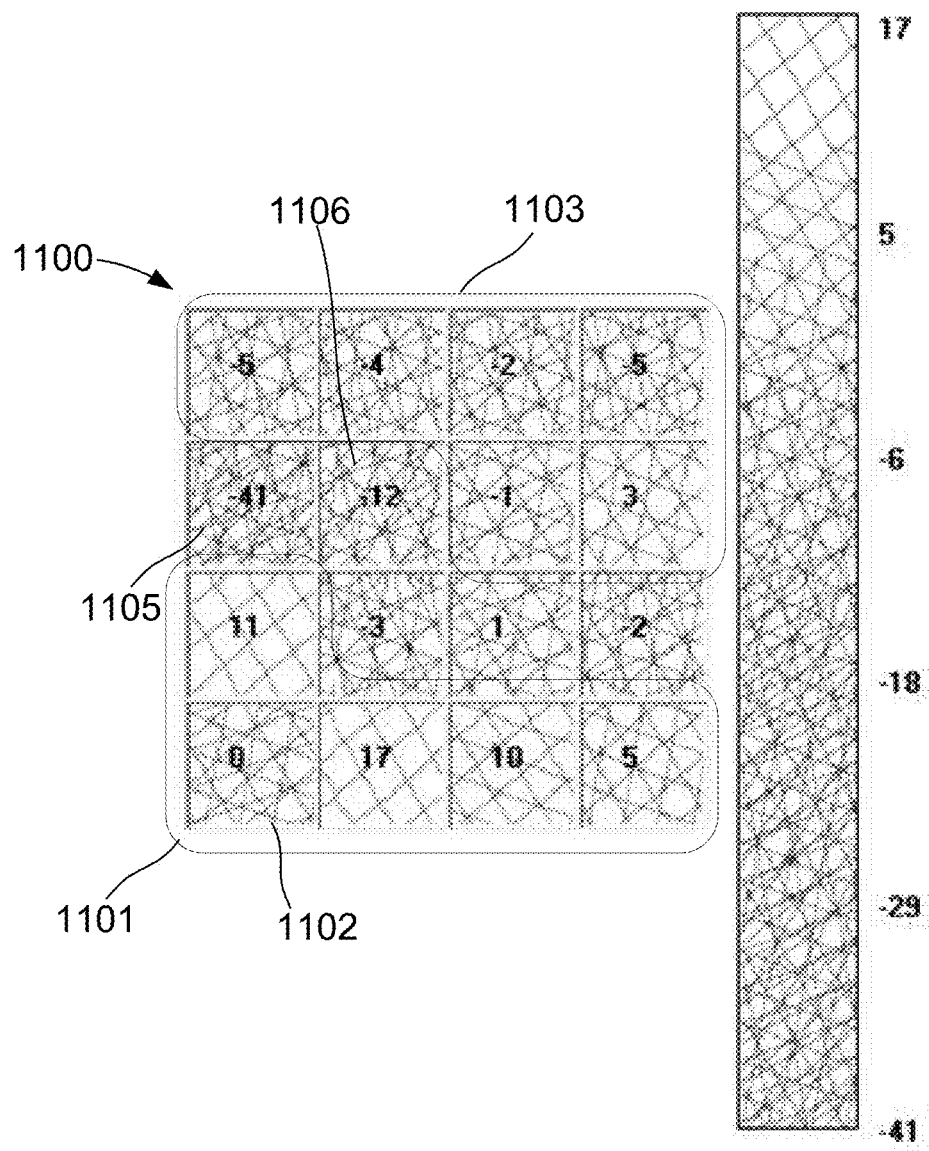
FIG. 11 is a schematic diagram of an example impedance difference map for use in identifying a tissue anomaly.

An example of this will now be described with reference to FIG. 11. For the purpose of this example, the impedance map of plasma with introduced red blood cells shown in FIG. 10 was used. In this example, the smaller maps 1001, 1003 are averaged, as are maps 1002, 1004, with the difference between these resulting maps being shown in the map 1100 of FIG. 11.

In this example, a region 1101 is highlighted which has low positive values of $R_0$, where dispersed blood is present, and this is due to different haematocrits being located under each of these electrode sets. Within this region, the site 1102 has an $R_0$ value of zero due to a high but homogeneous haematocrit sample being located under the electrode set.

In an upper right region 1103 of the impedance map, the average $R_0$ values are close to zero due to the sample under the electrode sets being homogeneous plasma, the red blood cells having not dispersed into this region.

At the site 1105, a large negative value of $R_0$ is present, implying the presence of a tissue anomaly or lesion. The site 1106 is also negative, but not to such a degree. This implies that a tissue anomaly is likely to be present at the site 1105 and that this may extend slightly into the site 1106. Accordingly, it will be appreciated that this not only allows tissue anomalies to be identified, but also allows the extent and/or boundaries of the tissue anomaly to be determined.

Figure 12A:
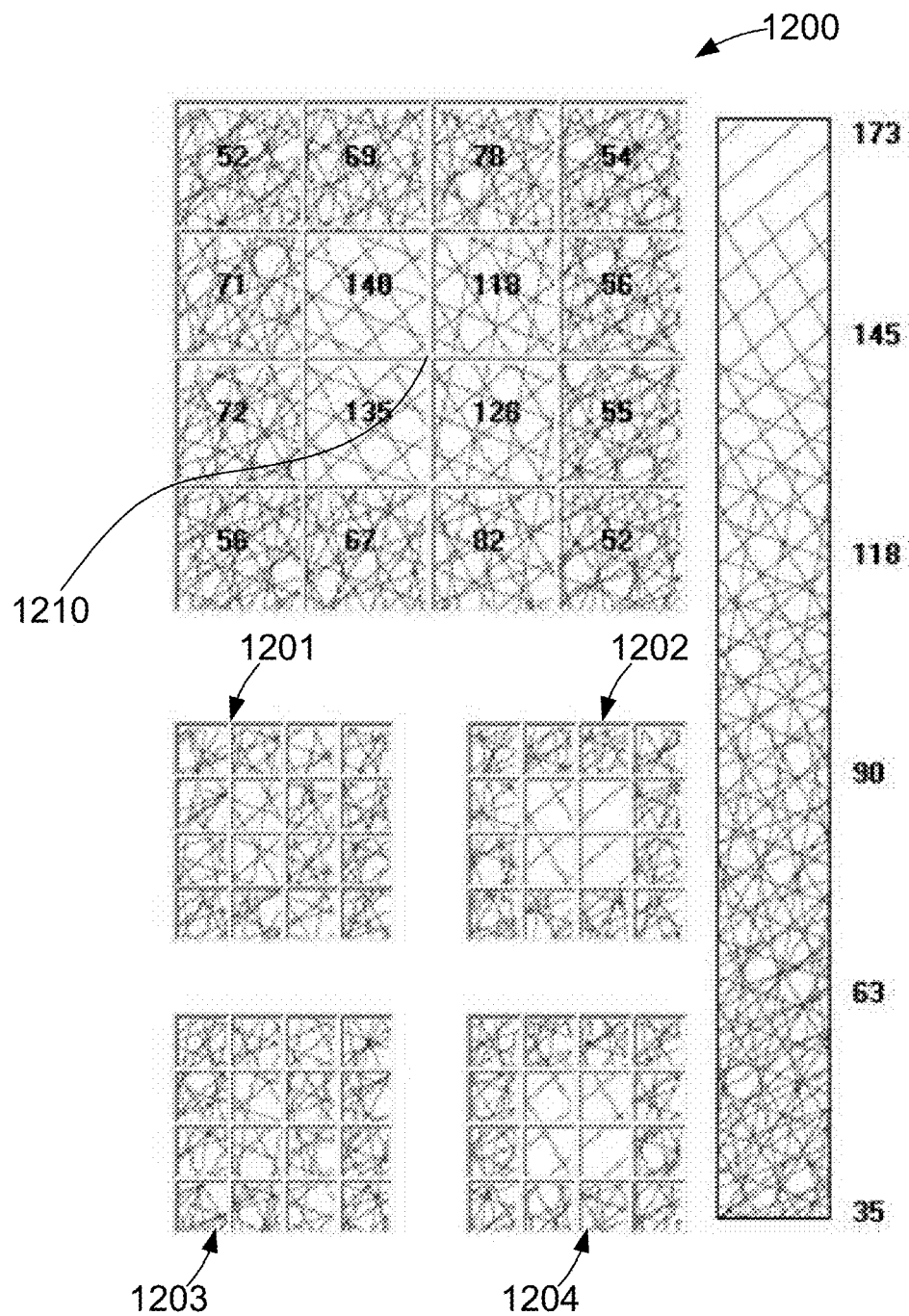
FIG. 12A is a schematic diagram of example impedance maps for plasma with an introduced red blood cell clot covering a central electrode.
Figure 12B:
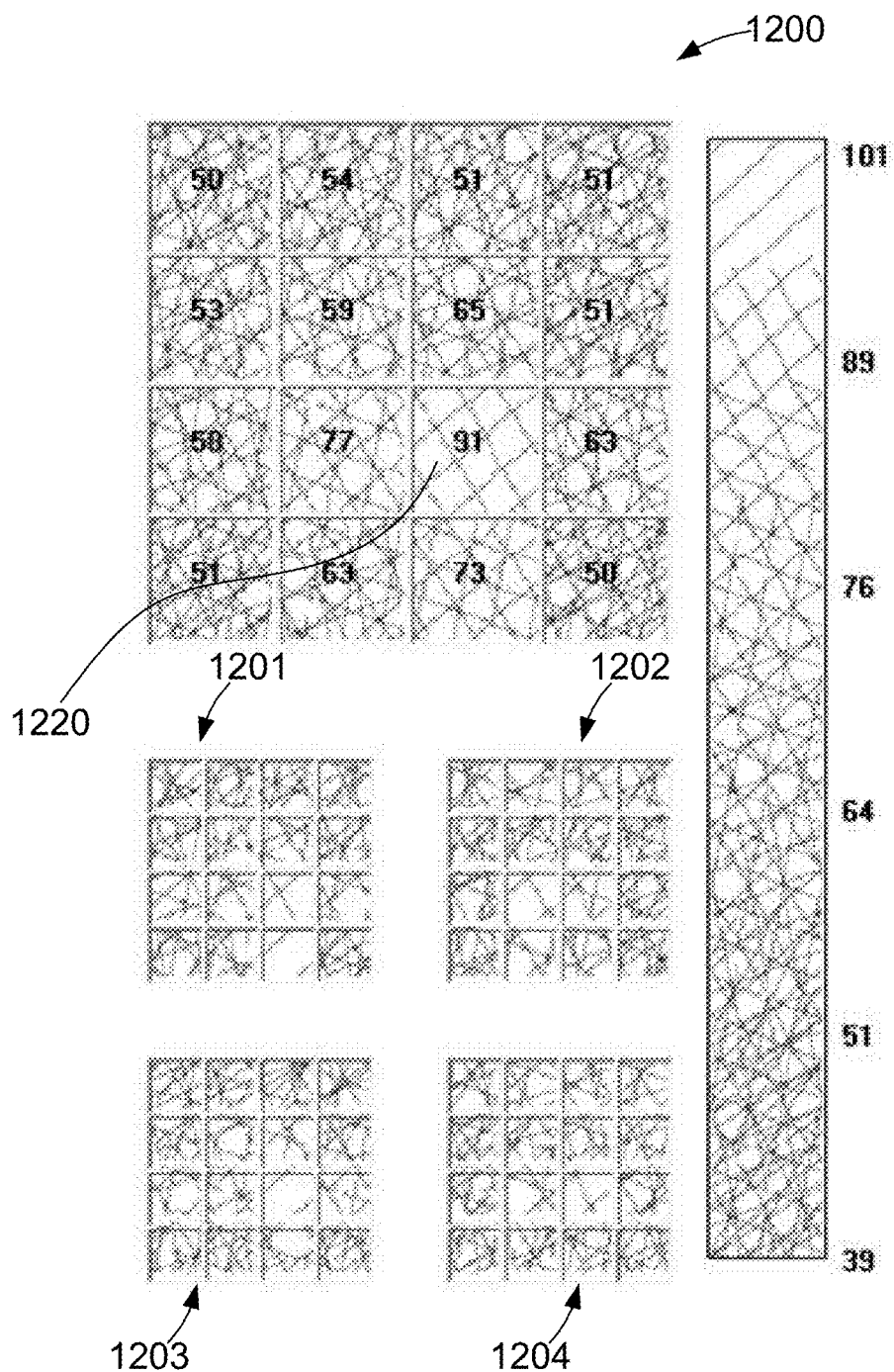
FIG. 12B is a schematic diagram of example impedance maps for plasma with an introduced red blood cell clot covering four electrodes associated with a respective measurement site; and, FIG. 12C is a schematic diagram of example impedance maps for plasma with an introduced red blood cell clot covering two measurement sites.
Figure 12C:
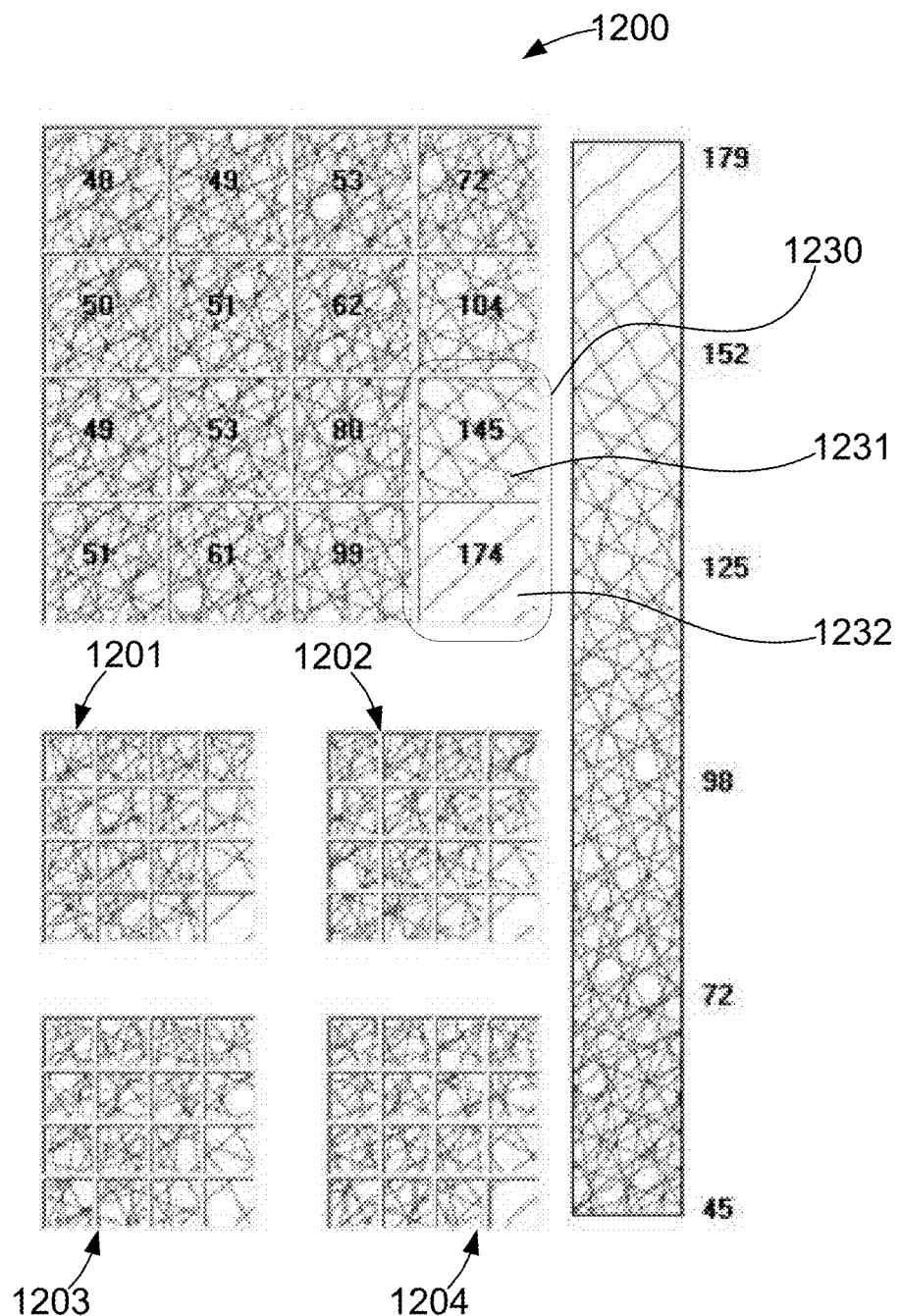

In a third example, a clot was introduced to the plasma in place of the red blood cells. FIGS. 12A, to 12C, display typical impedance maps 1200 with clots introduced in various regions on the electrode array. In the example of FIGS. 12A to 12C, the average value of $R_0$ obtained for each site is shown at 1200, with the four smaller maps 1201, 1202, 1203, 1204, corresponding to the impedance values for $R_0$ measured using respective electrode configurations, as shown for example in FIGS. 6A to 6D.

In FIG. 12A, the clot is introduced beneath a central electrode, the location of which is shown at 1210. In FIG. 12B, the clot is located at the site 1220, whilst in the example of FIG. 12C, the clot is provided in the region 1230, encompassing the sites 1231, 1232. These examples show clear impedance changes at the boundaries of the red blood cell clots due to minimal dispersion of red blood cells. This highlights how in practice the process can be used to identify the size of tissue anomalies, such as lesions and monitor their growth or change in shape over time.

It will therefore be appreciated that the above described methods provide techniques for identifying the presence, absence and even extent of tissue anomalies, such as lesions. These anomalies did not appear to alter the resultant impedance map once averaged, meaning that the averaging of results prevents the tissue anomalies being detected. However, this does mean that even in the event that anomalies exist, this avoids the need to remove and discard such measurements.

Thus, the above described techniques provide a non-subjective method for determining lesion size and hence possible biopsy margins.

By using an electrode array coupled to a suitable switching system, this allows measurements to be rapidly performed over an area of the subject. Furthermore, by using only two measurements at each site, this can reduce the number of measurements required at each region and minimise the time taken to acquire an impedance map.

Persons skilled in the art will appreciate that numerous variations and modifications will become apparent. All such variations and modifications which become apparent to persons skilled in the art, should be considered to fall within the spirit and scope that the invention broadly appearing before described.

Thus, for example, it will be appreciated that features from different examples above may be used interchangeably where appropriate. Furthermore, whilst the above examples have focussed on a subject such as a human, it will be appreciated that the measuring device and techniques described above can be used with any subject such as an animal, including but not limited to, primates, livestock, performance animals, such race horses, or the like, as well as to in-vitro samples, or the like.

The above described processes can be used for determining the health status of an individual, including determining the presence, absence or degree of a range of biological anomalies. It will be appreciated from this that whilst the above examples use the term lesion, this is for the purpose of example only and is not intended to be limiting.

Furthermore, whilst the above described examples have focussed on the application of a current signal to allow a voltage to be measured, this is not essential and the process can also be used when applying a voltage signal to allow a currant to be sensed.

The above described impedance maps are determined based on the value of the impedance parameter $R_0$. However, it will be appreciated that impedance maps based on other impedance parameters, such as actual measured impedances, or values of $R_\infty$, $Z_c$, or the like.

We claim:

1. Apparatus for use in performing impedance measurements on a subject, the apparatus comprising:
   a) an electrode array having a number of electrodes configured to form a rectangular array;
   b) a signal generator for generating signals to be applied to the subject using drive electrodes of the array;
   c) a sensor for determining measured signals induced across the subject using measurement electrodes of the array;
   d) a switching device coupled to the electrode array; and,
   e) a processing system that controls the switching device to selectively interconnect the signal generator and the sensor to the selected ones of the electrodes, which therefore function as drive and measurement electrodes, the processing system configured to control the switching device to:
     cause a first measurement to be performed at a first site using first and second electrodes as drive electrodes and using third and fourth electrodes as measurement electrodes;
     cause a second measurement to be performed at the first site using first and third electrodes as drive electrodes and using second and fourth electrodes as measurement electrodes;
     determine a presence, absence or degree of an anomaly at the first site using the first and second measurements;
     cause a third measurement to be performed at a second site using third and fifth electrodes as drive electrodes and using fourth and sixth electrodes as measurement electrodes;
     cause a fourth measurement to be performed at the second site using third and fourth electrodes as drive electrodes and using fifth and sixth electrodes as measurement electrodes; and
     determine a presence, absence or degree of an anomaly at the second site using the third and fourth measurements.

2. The apparatus according to claim 1, wherein the switching device is a multiplexer.

3. The apparatus according to claim 1, wherein the electrodes in the electrode array are configured to form a square grid.

4. The apparatus according to claim 1, wherein the electrodes have a diameter of approximately 1 mm.

5. The apparatus according to claim 1, wherein the electrode array is configured to form at least one of:
   a) a 2×2 array;
   b) a 2×4 array; and,
   c) a 5×5 array.

6. The apparatus according to claim 1, wherein a spacing between adjacent electrodes is at least one of:
   a) less than the diameter of the electrodes;
   b) fixed; and,
   c) approximately 0.77 mm.

7. The apparatus according to claim 1, wherein the processing system includes a processor, a memory, an input/output device and an external interface coupled together via a bus.

8. The apparatus according to claim 1, wherein the processing system is an FPGA.

9. The apparatus according to claim 1, wherein the processing system:
   a) determines a first impedance value, measured at a site using a first tetrapolar electrode configuration of drive and measurement electrodes selected from the array;
   b) causes at least one of the drive electrodes to become a measurement electrode and at least one of the measurement electrodes to become a drive electrode to thereby define a second tetrapolar electrode configuration by controlling the switching device;
   c) determines a second impedance value, measured at the site using the second electrode configuration
   d) determines a difference between the first and second impedance values; and,
   e) determines a presence, absence or degree of an anomaly using the determined difference.

10. The apparatus according to claim 1, wherein the processing system:
    a) controls the signal generator to apply one or more drive signals to the subject; and,
    b) receives an indication of the measured signals measured using the sensor.

11. The apparatus according to claim 1, wherein the processing system:
    a) receives an indication of drive signals applied to the subject;
    b) receives an indication of measured signals determined using the sensor; and,
    c) uses the indications to determine an impedance.

12. The apparatus according to claim 1, wherein the processing system controls the switching device to:
    a) cause a first measurement to be performed at the site using first and second electrodes as drive electrodes and using third and fourth electrodes as measurement electrodes; and,
    b) cause a second measurement to be performed at the site using first and third electrodes as drive electrodes and using second and fourth electrodes as measurement electrodes.

13. The apparatus according to claim 1, wherein the processing system controls the switching device to:
    a) cause a measurement to be performed at a site using first and second electrodes as drive electrodes and using third and fourth electrodes as measurement electrodes; and,
    b) cause a measurement to be performed at a second site using at least two of the first, second, third and fourth electrodes.

14. The apparatus according to claim 1, wherein the processing system forms part of a measuring device for performing impedance measurements.

15. The apparatus according to claim 9, wherein the processing system:
    a) determines impedance values at a number of different sites; and,
    b) determines an impedance map using the impedance values at each site.

16. The apparatus according to claim 15, wherein the processing system selects a different site by controlling the switching device to interconnect the signal generator and sensor to a different combination of four electrodes than used to perform impedance measurements at a previous site.

17. The apparatus according to claim 15, wherein the processing system:
   a) determines the presence of an anomaly at any one of the sites; and,
   b) determines the impedance map taking the anomaly into account.

18. The apparatus according to claim 17, wherein the processing system, for any site having an anomaly, at least one of:
   a) excludes the site from the impedance map;
   b) modifies the impedance value determined for the site.

19. The apparatus according to claim 18, wherein fluid levels in a region of the body are able to be determined from the impedance map taking into account any erroneous measurements caused by the anomaly.

20. The apparatus according to claim 9, wherein the processing system:
   a) determines a difference between the first and second impedance values;
   b) compares the difference to a reference; and,
   c) determines an anomaly depending on the result of the comparison.

21. The apparatus according to claim 20, wherein the reference is a previously measured difference value for the subject.

* * * * *